United States Patent
Park et al.

(10) Patent No.: US 9,364,556 B2
(45) Date of Patent: *Jun. 14, 2016

(54) DRUG CONJUGATE COMPRISING DRUG LINKED TO HUMAN C-MET ANTIBODY, AND USE THEREFOR

(71) Applicants: Korea Research Institute of Bioscience and Biotechnology, Daejeon (KR); A&RT Co., Ltd., Daejeon (KR)

(72) Inventors: Young Woo Park, Daejeon (KR); Ki Won Jo, Daejeon (KR); Sun Jeong Jo, Daejeon (KR); Soon Sil Hyun, Daejeon (KR); Jae Eun Park, Daejeon (KR); Seok Ho Yoo, Daejeon (KR); Myeoung Hee Jang, Daejeon (KR); Hye Nan Kim, Daejeon (KR); Chan Woong Park, Gwangju (KR)

(73) Assignees: Korea Research Institute of Bioscience and Biotechnology, Dajeon (KR); A&RT Co., Ltd., Daejeon (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/360,937

(22) PCT Filed: Nov. 28, 2012

(86) PCT No.: PCT/KR2012/010189
§ 371 (c)(1),
(2) Date: Sep. 28, 2014

(87) PCT Pub. No.: WO2013/081379
PCT Pub. Date: Jun. 6, 2013

(65) Prior Publication Data
US 2015/0110815 A1    Apr. 23, 2015

(30) Foreign Application Priority Data

Nov. 28, 2011    (KR) .......................... 10-2011-0125255

(51) Int. Cl.
*A61K 39/395*    (2006.01)
*A61K 47/48*    (2006.01)
*C07K 16/28*    (2006.01)
*A61K 31/704*    (2006.01)
*A61K 39/00*    (2006.01)

(52) U.S. Cl.
CPC ......... *A61K 47/48407* (2013.01); *A61K 31/704* (2013.01); *A61K 47/48561* (2013.01); *C07K 16/2803* (2013.01); *C07K 16/2863* (2013.01); *A61K 2039/505* (2013.01)

(58) Field of Classification Search
None
See application file for complete search history.

(56) References Cited

FOREIGN PATENT DOCUMENTS

| EP | 2143441 | 1/2010 |
|---|---|---|
| KR | 10-2011-0037932 | 4/2011 |
| KR | 10-2011-0043548 | 4/2011 |
| KR | 10-2011-0097839 | 8/2011 |
| WO | WO 2009/117096 | 9/2009 |
| WO | WO 2010/069765 | 6/2010 |
| WO | WO 2013/081379 | 6/2013 |

OTHER PUBLICATIONS

Strome et al., The Oncologist, 2007; 12:1084-95.*
Brand et al., Anticancer Res. 2006; 26:463-70.*
Chmielowiec et al. "C-Met Is Essential for Wound Healing in the Skin", The Journal of Cell Biology, 177(1): 151-162, Apr. 9, 2007.
Comoglio et al. "Drug Development of MET Inhibitors: Targeting Oncogene Addiction and Expedience", Nature Reviews Drug Discovery, 7: 504-516, Jun. 2008.
Huh et al. "Hepatocyte Growth Factor / C-Met Signaling Pathway Is Required for Efficient Liver Regeneration and Repair", Proc. Natl. Acad. Sci. US, PNAS, 101(13): 4477-4482, Mar. 30, 2004.
Jiang et al. "Hepatocyte Growth Factor, Its Receptor, and Their Potential Value in Cancer Therapies", Critical Reveiws in Oncology/Hematology, 53: 35-69, 2005.
Jin et al. "MetMab, the One-Armed 5D5 Anti-C-Met Antibody, Inhibits Orthotopic Pancreatic Tumor Growth and Improves Survival", Cancer Research, 68(11): 4360-4368, Jun. 1, 2008.
Nakamura et al. "Molecular Cloning and Expression of Human Hepatocyte Growth Factor", Nature, 342: 440-443, Nov. 23, 1989.
Nakamura et al. "Myocardial Protection From Ischemia/Reperfusion Injury by Endogenous and Exogenous HGF", The Journal of Clinical Investigation, 106(12): 1511-1519, Dec. 2000.
Novak et al. "Hepatocyte Growth Factor/Scatter Factor Is a Neurotrophic Survival Factor for Lumbar But Not for Other Somatic Motoneurons in the Chick Embryo", The Journal of Neuroscience, 20(1): 326-337, Jan. 1, 2000.
Sadelain "T-Cell Engineering for Cancer Immunotherapy", The Cancer Journal, 15(6): 451-455, Nov./Dec. 2009.
Tamagnone et al.o "Control of Invasive Growth by Hepatocyte Growth Factor (HGF) and Related Scatter Factors", Cytokine & Growth Factor Reviews, 8(2): 129-142, 1997.
International Search Report and the Written Opinion Dated Mar. 18, 2013 From the Korean Intellectual Property Office Re. Application No. PCT/KR2012/010189 and Its Translation of the Search Report Into English.
Leo "Immunoglobulin Lambda Light Chain, Partial [*Homo sapiens*]", NCBI Database [Online], GenBank: CAA67402.1, Database Accession No. CAA67402, Nov. 25, 1998.
Pasqualucci et al. "Immunoglobulin Heavy Chain VDJ Region, Partial [*Homo sapiens*]", NCBI Database [Online], GenBank: AAG25648.1, Database Accession No. AAG25648, Mar. 23, 2001.

* cited by examiner

Primary Examiner — Sheela J Huff

(57) ABSTRACT

The present invention relates to a drug conjugate comprising a cytotoxic drug conjugated to a c-Met specific human antibody. More specifically, the present invention relates to: a drug conjugate comprising a cytotoxic drug conjugated to a c-Met specific human antibody; a pharmaceutical composition for cancer treatment comprising the drug conjugate; and a cancer treatment method comprising a step in which the drug conjugate or pharmaceutical composition is administered to an individual.

16 Claims, 20 Drawing Sheets

Fig. 2
Bst NI-Digestion (in 8% Acrylamide gel)
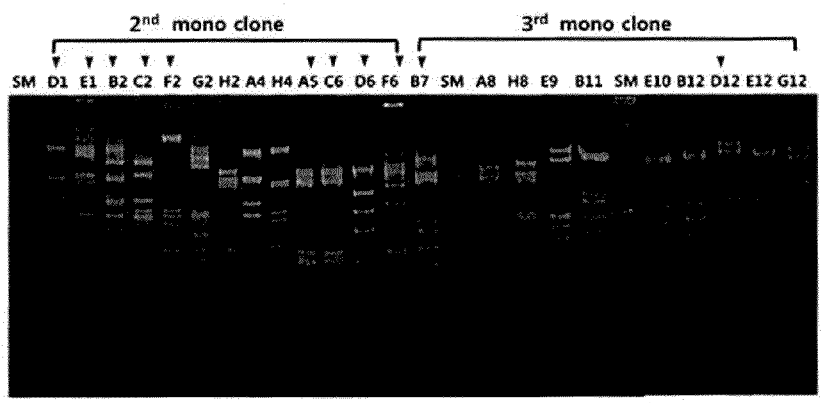
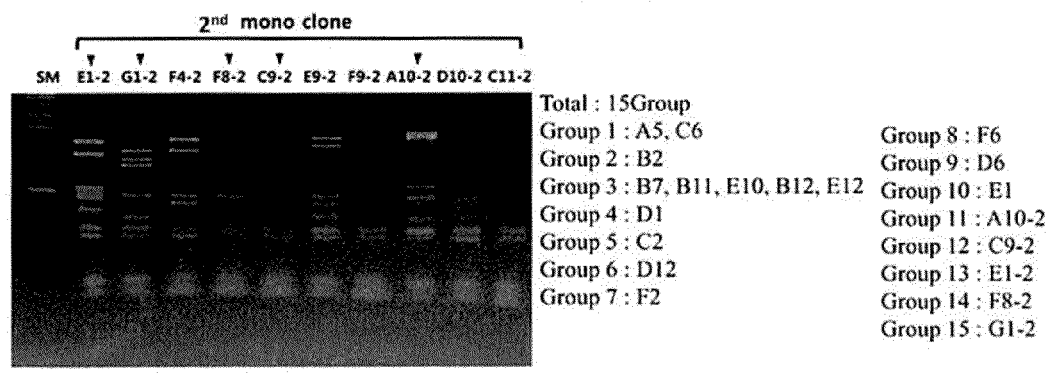
Total : 15Group
Group 1 : A5, C6
Group 2 : B2
Group 3 : B7, B11, E10, B12, E12
Group 4 : D1
Group 5 : C2
Group 6 : D12
Group 7 : F2
Group 8 : F6
Group 9 : D6
Group 10 : E1
Group 11 : A10-2
Group 12 : C9-2
Group 13 : E1-2
Group 14 : F8-2
Group 15 : G1-2

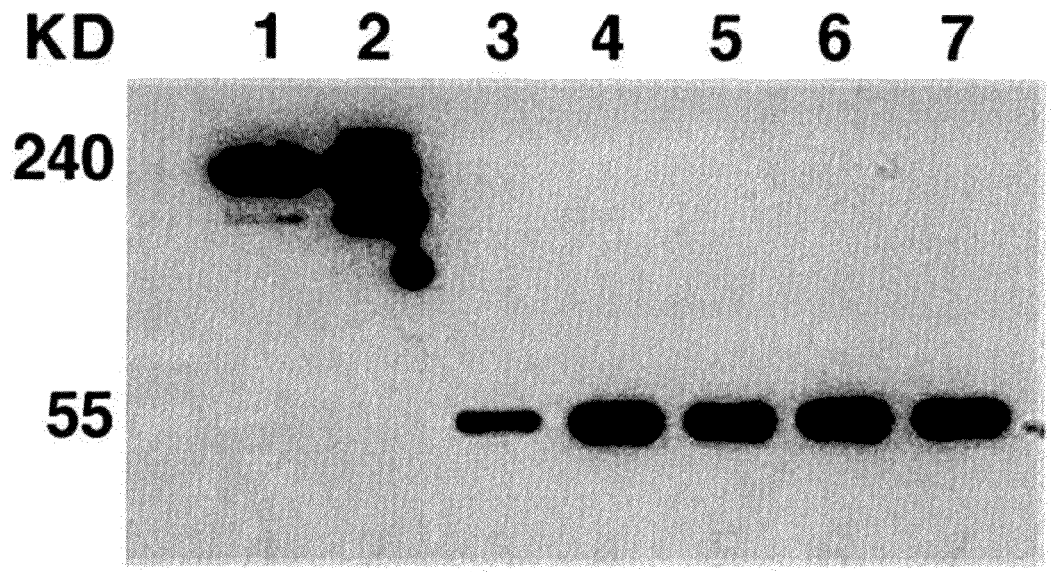

|  | ug/ul | volume | total(mg) |
|---|---|---|---|
| S#1 | 1.06 | 1ml | 1.06mg |
| S#2 | 1.28 | 1ml | 1.28mg |

1st lane; 100 bp ladder marker
2nd lane; 5 µL of reaction mixture
3rd lane; 10 µL of reaction mixture 1st lane; 100 bp ladder marker
2nd lane; intact pNATAB Heavy chain vector
3rd lane; restriction enzyme (Sfi I and NheI)
    reacted pNATAB Heavy chain vector
4th lane; 100 bp ladder marker
5th lane; insert DNA
6th lane; restriction enzyme (Sfi I and NheI)
    reacted insert DNA 1st lane; Human IgG 0.5 μg non reducing
2nd lane; Human IgG 1 μg non reducing
3rd lane; Human IgG 2 μg non reducing
4th lane; B7-modified 2 μg non reducing
5th lane; protein ladder marker
6th lane; Human IgG 0.5 μg reducing
7th lane; Human IgG 1 μg reducing
8th lane; Human IgG 2 μg reducing
9th lane; B7-modified 2 μg reducing 1st lane; protein ladder marker
2nd lane; modified B7 reducing
3rd lane; modified B7 non reducing
4th lane; reduction with 100 equiv of TCEP
5th lane;reduction with 1000 equiv of TCEP
6th lane; oxidation with 4 equiv of dhAA to 100 equiv of TCEP
7th lane; oxidation with 20 equiv of dhAA to 100 equiv of TCEP

DRUG CONJUGATE COMPRISING DRUG LINKED TO HUMAN C-MET ANTIBODY, AND USE THEREFOR

RELATED APPLICATIONS

This application is a National Phase of PCT Patent Application No. PCT/KR2012/010189 having International filing date of Nov. 28, 2012, which claims the benefit of priority of Korean Patent Application No. 10-2011-0125255 filed on Nov. 28, 2011. The contents of the above applications are all incorporated by reference as if fully set forth herein in their entirety.

SEQUENCE LISTING STATEMENT

The ASCII file, entitled 59573SequenceListing.txt, created on Aug. 14, 2014, comprising 15,281 bytes, submitted concurrently with the filing of this application is incorporated herein by reference.

TECHNICAL FIELD

The present invention relates to an antibody-drug conjugate comprising a cytotoxic drug conjugated to a c-Met-specific human antibody, and more specifically to an antibody-drug conjugate comprising a cytotoxic drug conjugated to a c-Met-specific human antibody, a pharmaceutical composition for treating cancer, which comprises the antibody-drug conjugate, and a method for treating cancer, which comprises administering the antibody-drug conjugate or the pharmaceutical composition to a subject.

BACKGROUND ART

Hepatocyte Growth factor/scattering factor (HGF/SF) is a pleiotropic cytokine that performs various functions in developmental processes. HGF/SF binds to its receptor c-Met tyrosine kinase to induce various bioreactions including the migration, invasion, proliferation, survival and morphological change of target cells (Jiang et al., Critical Reviews in Oncology/Hematology. 53:35-69, 2005). HGF/SF is a cytokine of mesenchymal origin and was reported to act on hepatocytes and other epithelial cells including endothelial cells, melanocytes, hematopoietic cells and osteocytes, to activate the above reactions through its receptor c-Met (Tamagnone and Comoglio, Cytokine & Growth factor Rev. 8:129-142, 1997).

The present inventors previously reported that the deregulation of HGF/SF-Met signaling does not influence the usual function of hepatocytes, but adversely affects the regeneration of damaged hepatocytes. Since then, the present inventors confirmed that, when the skin in addition to the liver is damaged, HGF/SF and c-Met are secreted. In other words, large amounts of HGF/SF and c-Met are secreted from hyperproliferative skin tissue to promote the proliferation of skin cells. However, it was reported that c-Met is found in the skin and hair follicles, whereas HGF/SF is usually expressed only in hair follicles and is found in skin that is damaged. Thus, HGF/SF remains in an inactivated state until the skin is damaged, and it is activated around wounds after the skin is damaged (Journal of Cell Biology 177(1):151-162, 2007). Accordingly, it is known that HGF/c-Met directly regulates skin regeneration and repair (Nakamura et al., Nature. 342: 440-443, 1993; Huh et al., Proc Natl Acad Sci USA. 101: 4477-4482, 2004).

In vitro and in vivo studies indicated that HGF/SF also acts on the nervous system, and many studies on the function of HGF/SF to protect motor neurons were reported (Novak et al., Journal of Neuroscience. 20:326-337, 2000). In addition, it was suggested that HGF/SF plays an important role in defensive physiological mechanisms following general organ damage such as heart damage (Nakamura et al., J Clin Invest. 106:1511-1519, 2000). Indeed, it was demonstrated that the HGF/MET pathway is involved in the processes of neural infraction, progressive nephritis, liver cirrhosis and pulmonary fibrosis and that HGF is overexpressed in lesions of such degenerative diseases to exhibit a defensive physiological activity of protecting tissue from damage (Comoglio et al., Nature Review Drug Discovery. 7:504-516, 2008).

Therefore, it has been suggested that HGF/SF can be developed as an agent for preventing the death of neural cells in the central nervous system, an agent for treating neurodegenerative diseases, including Parkinson's disease, ischemia leading to nervous infarction and Alzheimer's disease, and a regenerative therapeutic agent that is used after the occurrence of damage to the heart, the kidneys, the liver and the lungs, as well as ulcerative wounds.

The excessive activity of HGF/c-Met signaling is associated with tumorigenesis of various endothelial cells and angiogenesis, and from this point of view, it was suggested that an antagonistic c-Met antibody that targets c-Met can be used as an anticancer agent (Comoglio et al., Nature Review Drug Discovery. 7:504-516, 2008). For example, it was reported that a one-armed c-Met antibody efficiently inhibits tumor growth in a transplanted mouse model by negatively regulating the activation of HGF caused by dimerization of c-Met (Jin et al, Cancer Research 68(11): 4360-4368, 2008; Comoglio et al., Nature Review Drug Discovery. 7:504-516, 2008). In addition, in T-cell therapy, an antibody to an antigen that is overexpressed in cancer cells is used in tumor targeting for linking of T cells in the genetic manipulation of T cells that selectively recognizes a cancer cell surface antigen (Sadelain, The Cancer Journal 15(6):451-455, 2009). However, it was not reported that agonistic antibodies against c-Met can be used as alternatives for anticancer agents.

Meanwhile, the cytotoxic drug doxorubicin that is used as an anticancer agent, and the like, targets the cell cycle, and thus the toxicity thereof is dependent on the proliferation of cancer cells. Also, these drugs are used in the highest acceptable amounts to provide clinical therapeutic effects. However, it has been reported that such anticancer agents merely kill rapidly proliferating cells, cannot distinguish normal cells from cancer cells or cancer tissues to kill cells other than cancer cells, and cause side effects such as vomiting when being used at high concentrations. In addition, these anticancer agents can cause resistance to anticancer agents when being used for a long period of time. For these reasons, there is an urgent need for an improved therapy in which a cytotoxic drug targets and kills only cancer cells. In addition, conventional drugs have a disadvantage in that their therapeutic effects are reduced in hypoxic tumor conditions in which the level of oxygen decreases as a tumor grows.

DISCLOSURE

Technical Problem

The present inventors have made extensive efforts to find a method that enables a cytotoxic drug to be delivered specifically to cancer cells and that allows a cytotoxic drug to exhibit its effect in cancer cells. As a result, the present inventors have developed a novel antibody-drug conjugate comprising doxorubicin conjugated to an agonistic antibody against c-Met and have found that the novel antibody-drug conjugate specifically inhibits the growth of cancer cells even at a concentration lower than the concentration at which conventional doxorubicin shows toxicity, thereby completing the present invention.

Technical Solution

It is an object of the present invention to provide an antibody-drug conjugate comprising a cytotoxic drug conjugated to a c-Met-specific human antibody.

Another object of the present invention is to provide a pharmaceutical composition for treating cancer, which comprising the antibody-drug conjugate.

Still another object of the present invention is to provide a method for treating cancer, which comprises administering the antibody-drug conjugate or the pharmaceutical composition to a subject.

Advantageous Effects

The antibody-drug conjugate according to the present invention comprises a c-Met-specific human antibody that enables a cytotoxic drug to act selectively in cancer cells in which c-Met was overexpressed, thereby reducing the occurrence of side effects. Further, the conjugate of the present invention enables a cytotoxic drug to act at a concentration lower than the concentration at which a conventional cytotoxic drug acts, making it possible to reduce the patient's pain. In addition, the conjugate of the present invention makes it possible to treat hypoxic tumors that have been difficult to treat by conventional drugs. Thus, the antibody-drug conjugate of the present invention will offer a new alternative for the anticancer drug markers.

DESCRIPTION OF DRAWINGS

FIG. 2 is electrophoresis photographs showing the results of fingerprinting for c-Met monoclonal phages.

FIG. 4 is a photograph showing the results of Western blot analysis performed to determine whether an antibody was expressed.

BEST MODE

Figure 1:
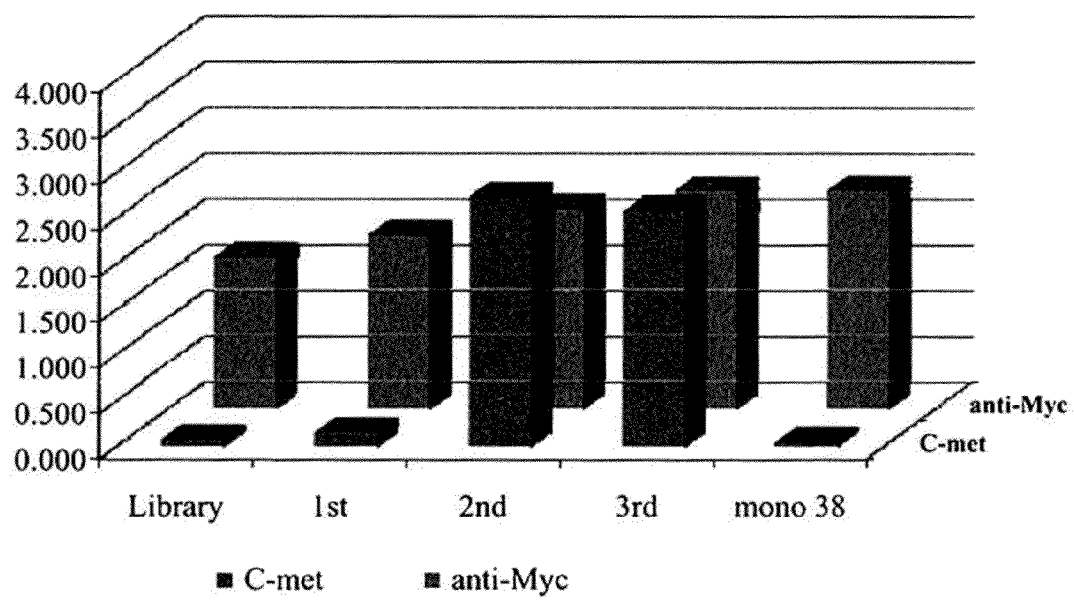
FIG. 1 is a graphic diagram showing the results of ELISA for c-Met polyclonal phage antibodies.

In one aspect, the present invention provides an antibody-drug conjugate comprising a cytotoxic drug conjugated to a c-Met-specific human antibody. Preferably, the c-Met-specific human antibody may comprise: a heavy-chain variable region comprising a heavy-chain CDR1 comprising amino acids having the sequence set forth in SEQ ID NO: 1, a heavy-chain CDR2 comprising amino acids having the sequence set forth in SEQ ID NO: 2, and a heavy-chain CDR23 comprising amino acids having the sequence set forth in SEQ ID NO: 3; and a light-chain variable region comprising a light-chain CDR1 comprising amino acids having the sequence set forth in SEQ ID NO: 4, a light-chain CDR2 comprising amino acids having the sequence set forth in SEQ ID NO: 5, and a light-chain CDR3 comprising amino acids having the sequence set forth in SEQ ID NO: 6.

As used herein, the term "CDR (complementarity determining region)" refers to a loop-shaped site involved in antigen recognition, and the specificity of an antibody against antigen depends on modification in that site.

As used herein, the term "c-Met" refers to a receptor of HGF (hepatocyte growth factor). For the purpose of the present invention, the term "c-Met" may be used interchangeably with Met or Met receptor. For the purpose of the present invention, the human antibody in the present invention can function to induce HGF/c-Met signaling and can also bind specifically to c-Met to function as a mimic of HGF and thus as an agonistic antibody. c-Met has a characteristic in that the expression thereof is more easily induced under hypoxic conditions. Thus, the c-Met-specific human antibody can bind specifically to hypoxic tumor cells or tissues.

As used herein, the term "c-Met-specific human antibody" may mean a human antibody capable of binding specifically to c-Met. A method for producing this human antibody and the sequences of this human antibody are disclosed in, for example, Korean Patent Application No. 10-2011-0054177.

In the present invention, the term "antibody" is meant to comprise not only a whole antibody but also a functional fragment of the antibody molecule. The whole antibody comprises two full length light chains and two full length heavy chains. Each light chain is linked to the heavy chain by a disulfide bond. In addition, the functional fragment of the antibody means a fragment having an antigen-binding function, including Fab, F(ab'), F(ab')2 and Fv. Among the antibody fragments, Fab has light-chain and heavy-chain variable regions, a light-chain constant region and a first heavy-chain constant region (CH1) and includes one antigen-binding region. Fab' differs from Fab in that it includes a hinge region including one or more cysteine residues at the C-terminal end of the heavy-chain CH1 domain. F(ab')2 antibody is produced when cysteine residues in the hinge region of Fab' form a disulfide bond. Fv is a minimal antibody fragment having only a heavy-chain variable region and a light-chain variable region, and gene recombination techniques for production of Fv fragments are disclosed in International Patent Publication Nos. WO 88/10649, WO 88/106630, WO 88/07085, WO 88/07086 and WO 88/09344. Double-stranded Fv (dsFv) has a configuration in which the heavy-chain variable region is linked to the light-chain variable region by a disulfide bond, and single-stranded Fv (scFv) generally has a configuration in which the heavy-chain variable region is covalently linked to the light-chain variable region by a peptide linker. These fragments can be produced using enzymes hydrolyzing proteins. For example, Fab can be obtained by cleaving the whole antibody with papain, and F(ab')2 can be obtained by cleaving the whole antibody with pepsin. Preferably, these antibody fragments can be produced by gene recombination techniques. The antibody that is used in the present invention is preferably in the form of Fab or whole antibody. For the purpose of the present invention, the human antibody may be a monoclonal antibody. Because all the elements of the human antibody in the present invention are of human origin, the human antibody has a low possibility of causing an immune reaction compared to conventional humanized antibodies or mouse antibodies. Thus, when the human antibody is administered to humans, it will not cause an undesired immune response, suggesting that it is highly useful as a therapeutic antibody.

Figure 11:
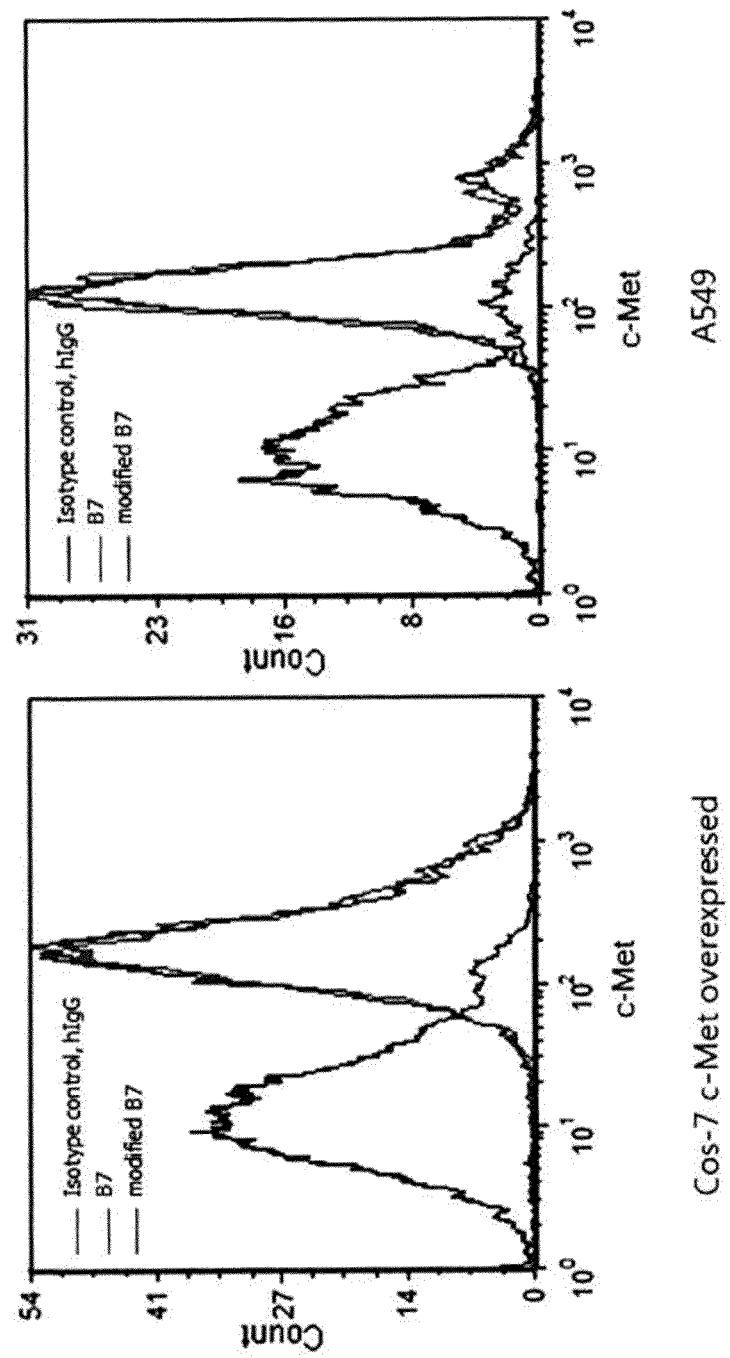
FIG. 11 shows the results of FACS performed to confirm whether modified B7 antibody binds specifically to c-Met.

Preferably, the c-Met-specific human antibody may further comprise a cysteine residue in the heavy-chain variable region. This added cysteine can be used as a functional group that reduces a disulfide bond to expose a free thiol group through which a drug is conjugated to the antibody. One or more cysteine residues may be added to the heavy-chain variable region and may be site-specifically coupled to a thiol-reactive reagent. Such cysteine residues may be linked to a linker so that the human antibody can be conjugated to a drug. Cysteine residues may be added to not only the heavy-chain variable region, but also the light-chain variable region or the heavy-chain or light-chain constant region, as long as they enable the human antibody to be effectively conjugated to a cytotoxic drug and, at the same time, do not reduce the ability of the human antibody to the target c-Met. In one example of the present invention, the results of FACS analysis indicated that c-Met-specific B7 antibody and a modified B7 antibody comprising added cysteine residue to the heavy-chain variable region of the B7 antibody all bind specifically to c-Met (FIG. 11). Such results support that the ability of the human antibody to bind to c-Met is not reduced even if the human antibody is modified by addition of cysteine, suggesting that cysteine can be used to conjugate the human antibody to a drug.

The c-Met-specific human antibody may comprise a heavy-chain variable region comprising amino acids having the sequence set forth in SEQ ID NO: 7 and a light-chain variable region comprising amino acids having the sequence set forth in SEQ ID NO: 11. Preferably, c-the Met-specific human antibody may comprise a heavy-chain region comprising amino acids having the sequence set forth in SEQ ID NO: 8, obtained by adding a cysteine residue to the heavy-chain variable region of SEQ ID NO: 7, and a light-chain variable region comprising amino acids having the sequence set forth in SEQ ID NO: 11.

Also, c-Met-specific human antibody may be a human antibody comprising a heavy-chain constant region comprising amino acids having the sequence set forth in SEQ ID NO: 13 and a light-chain constant region comprising amino acids having the sequence set forth in SEQ ID NO: 15. Preferably, it may be a human antibody composed of: a variable region comprising a heavy-chain variable region comprising amino acids having the sequence set forth in SEQ ID NO: 8, and a light-chain variable region comprising amino acids having the sequence set forth in SEQ ID NO: 11; and a constant region comprising a heavy-chain constant region comprising amino acids having the sequence set forth in SEQ ID NO: 13, and a light-chain constant region comprising amino acids having the sequence set forth in SEQ ID NO: 15.

The cytotoxic drug may be conjugated to the c-Met-specific human antibody by a linker. As the linker, any substance may be used without limitation, as long as it is stable in bloodstream to prevent the antibody from being separated from the drug during in vivo blood circulation so that the drug can be maintained in a prodrug state until it reaches its target, thereby minimizing damage to normal tissue. An example of the linker may be a hydrazone or a peptide linker. The hydrazone linker is obtained by the conversion of a carbonyl group ($>C=O$) into $>C=N-NH_2$ in a reaction between aldehyde, ketone and hydrazone. The hydrazone linker is unstable under acidic conditions, and thus is separated under acidic conditions so that the cytotoxic drug can be separated from the antibody to exhibit cytotoxicity. The peptide linker includes a linker that forms a peptide bond, and is cleaved by intracellular protease so that the cytotoxic drug can be separated from the antibody to exhibit cytotoxicity. The cytotoxic drug may be conjugated to the human antibody by a Schiff base.

As used herein, the term "Schiff base" refers to a compound having a functional group which has a carbon-nitrogen double bond ($C=N$) with the nitrogen atom connected to an aryl or alkyl group. The Schiff base may be represented by the formula $R^1R^2C=NR^3$. When the Schiff base is used, the nucleophilic functional group of the antibody attacks the electrophilic functional group of the linker to form a covalent bond. In the above formula, the R groups may be organic groups, including, but not limited to, hydrogen, alkyl, phenyl and the like.

The cytotoxic drug may preferably be conjugated to the human antibody by [linker-Val (valine)-Cit (citrulline)] or [linker-Schiff base]. This conjugation can be achieved by a covalent bond. The linker may be N-maleimidopropionamido-ethyleneglycol.

Figure 14:
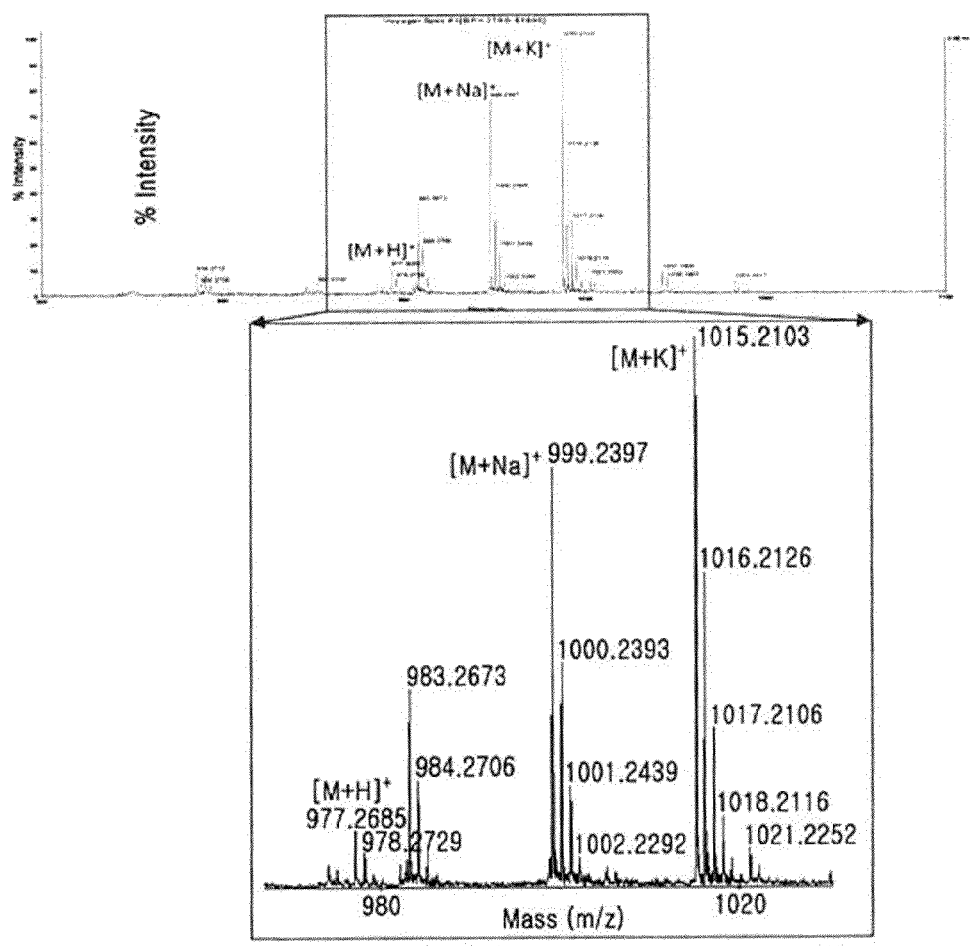
FIG. 14 shows the results of MALDI-TOF mass spectrometry of linker-Val-Cit-Glu.
Figure 15:
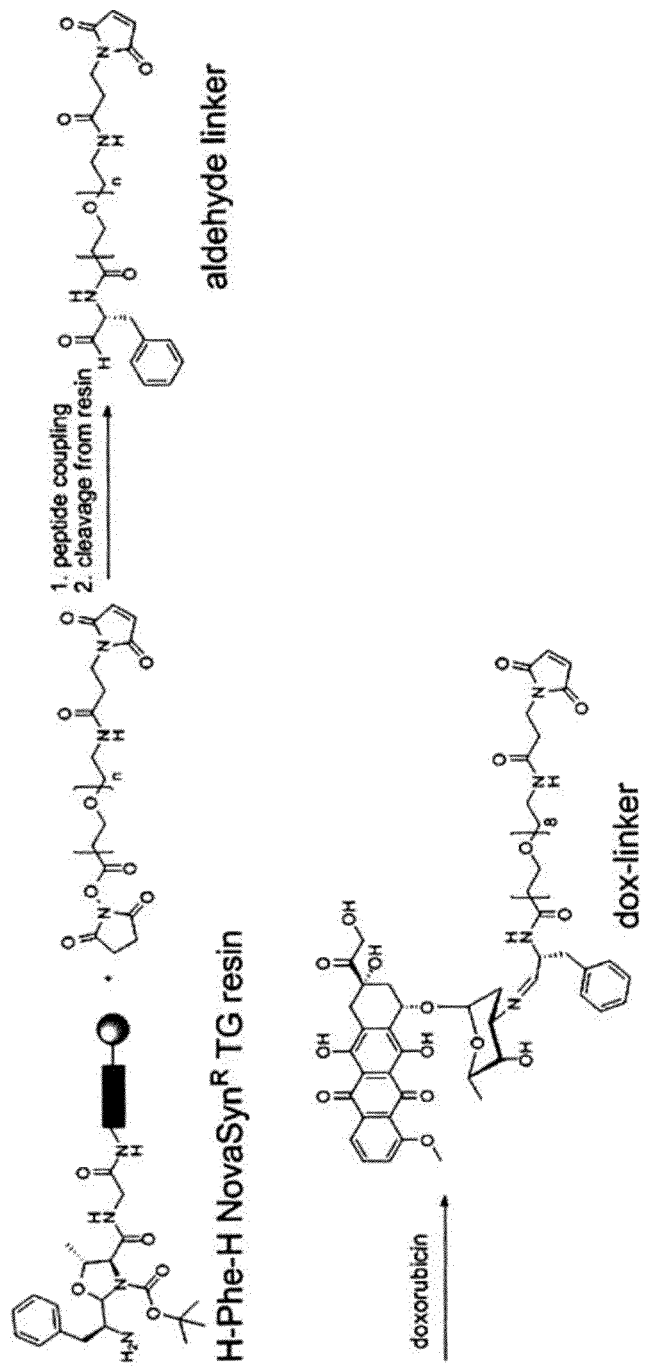
FIG. 15 schematically shows a process for synthesizing a doxorubicin derivative (dox-linker).

When the cytotoxic drug is conjugated to the human antibody by [linker-Val (valine)-Cit (citrulline)], it can be separated from the antibody by cleavage with an enzyme such as intracellular protease in vivo, and when the cytotoxic drug is conjugated to the human antibody by [linker-Schiff base], it can be cleaved and separated under acidic conditions in vivo. According to one embodiment of the present invention, in Example 4 a reaction in which the cytotoxic drug doxorubicin is conjugated to the antibody by [linker-Val (valine)-Cit (citrulline)] was carried out (FIGS. 12 to 14), and in Example 5, a reaction in which the cytotoxic drug doxorubicin is conjugated to the antibody by [linker-Schiff base] was carried out (FIG. 15).

Figure 17:
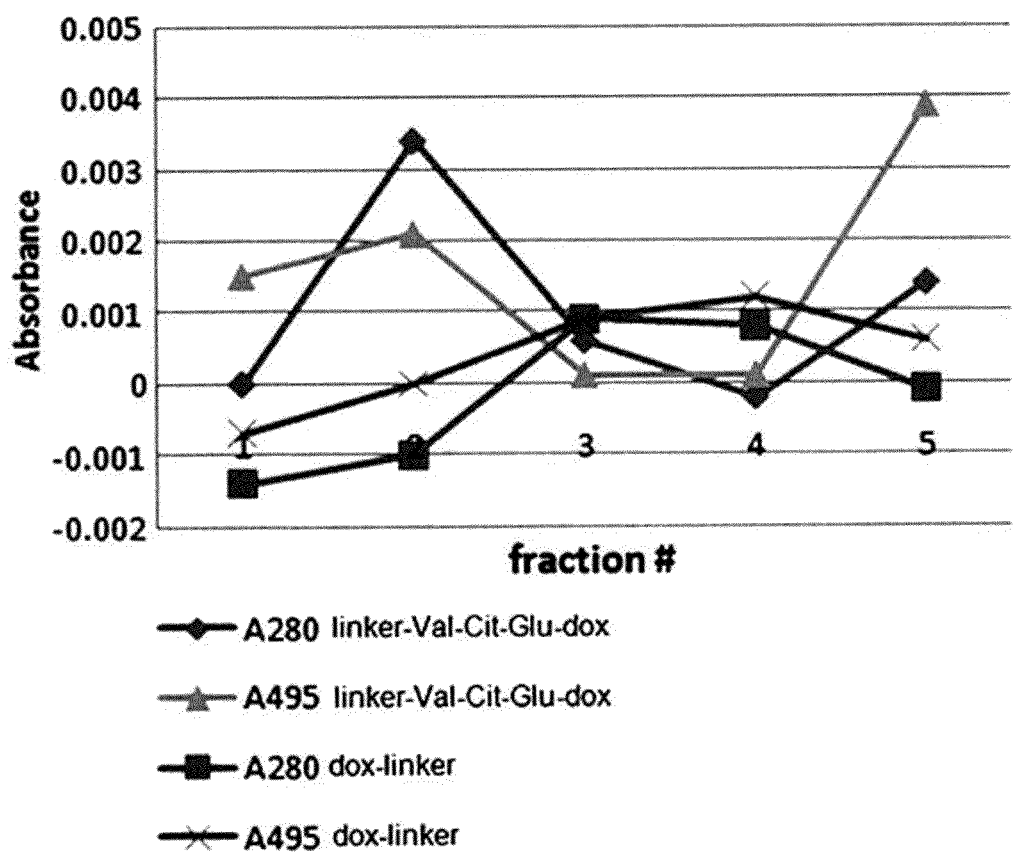
FIG. 17 shows the results of measuring the absorbance of doxorubicin-conjugated B7 antibodies purified by a protein A column.

After the cytotoxic drug was linked to [linker-Val (valine)-Cit (citrulline)] or [linker-Schiff base] by a covalent bond, the linked structure can be reacted with a thiol group exposed by reducing a disulfide bond in a c-Met-specific human antibody comprising a cysteine residue added thereto, thereby forming an antibody-drug conjugate. According to one embodiment of the present invention, it was found that doxorubicin was stably conjugated to a modified B7 antibody (FIG. 17).

As used herein, the term "cytotoxic drug" means any drug that can be used for the treatment of cancer. For example, the cytotoxic drug may be selected from the group consisting of doxorubicin, carboplatin (paraplatin), cisplatin, cyclophosphamide, ifosfamide, nidran, nitrogen mustard (mechlorethamine HCL), bleomycin, mitomycin C, cytarabine, fluorouracil, gemcitabine, trimetrexate, methotrexate, etoposide, vinblastine, vinorelbine, alimta, altretamine, procarbazine, taxol, taxotere, topotecan and irinotecan. Preferably, the cytotoxic drug may be doxorubicin.

In another aspect, the present invention provides a pharmaceutical composition for treating cancer, which comprises the antibody-drug conjugate.

As used herein, the term "treating" refers to all actions that alleviate or beneficially change symptoms of cancer disease by administering the composition of the present invention.

Cancer that can be treated by the present invention may be any cancer that can be selectively killed using the antibody-drug conjugate of the present invention. For example, the cancer may be cancer of the skin, digestive system, urinary system, reproductive system, respiratory system, circulatory system, brain or nerve system. Specifically, the cancer may be lung cancer, non-small cell lung cancer, colon cancer, bone cancer, pancreatic cancer, skin cancer, head or neck cancer, uterine cancer, ovarian cancer, rectal cancer, stomach cancer, anal cancer, breast cancer, cancer of fallopian tube, endometrial cancer, cervical cancer, vaginal cancer, vulva cancer, Hodgkin's disease, cancer of esophageal, small intestine cancer, endocrine cancer, thyroid cancer, parathyroid cancer, adrenal cancer, soft tissue sarcoma, urethral cancer, penis cancer, prostate cancer, chronic or acute leukemia, lymphocytic lymphoma, bladder cancer, kidney or ureter cancer, renal cell carcinoma, renal pelvic cancer, tumor of the central nervous system (CNS), primary central nervous system lymphoma, spinal-cord tumor, brain stem gliomas or pituitary adenoma. For the purpose of the present invention, the cancer may preferably be a cancer that expresses c-Met. The expression of c-Met increases under hypoxic conditions. Such hypoxic conditions are phenomena that occur in cancer due to the promotion of vascular production resulting from the proliferation of cancer cells. Thus, the cancer may more preferably be a hypoxic tumor. This hypoxic tumor has been difficult to treat with conventional drugs, but the composition of the present invention overcomes the shortcoming of conventional drugs by using a cytotoxic drug conjugated to a c-Met-specific antibody.

The pharmaceutical composition of the present invention may be characterized in that the antibody-drug conjugate is internalized into cells by endocytosis and the formation of clathrin-coated pits occurs. The antibody-drug conjugated internalized into cells is released from clathrin and fused with other vesicles in the cells, and then routed to the endosome-lysosome pathway. Then, the linker is cleaved by protease in the acidic environment of endosomes, and the activated free drug migrates to the cytoplasm through the lysosomal membrane, and then binds to its molecular target, whereby the cell cycle of cancer cells can be stopped and the cancer cells can be killed by apoptosis. This internalization by endocytosis is possible because the antibody of the present invention functions as an agonistic antibody.

The cytotoxic drug of the conjugate can be separated from the antibody either by intracellular protease or under an intracellular acidic condition to kill cancer cells or inhibit cancer cell growth, thereby treating cancer. This intracellular acidic condition may be a pH of 5.0 to 5.5.

Figure 18:
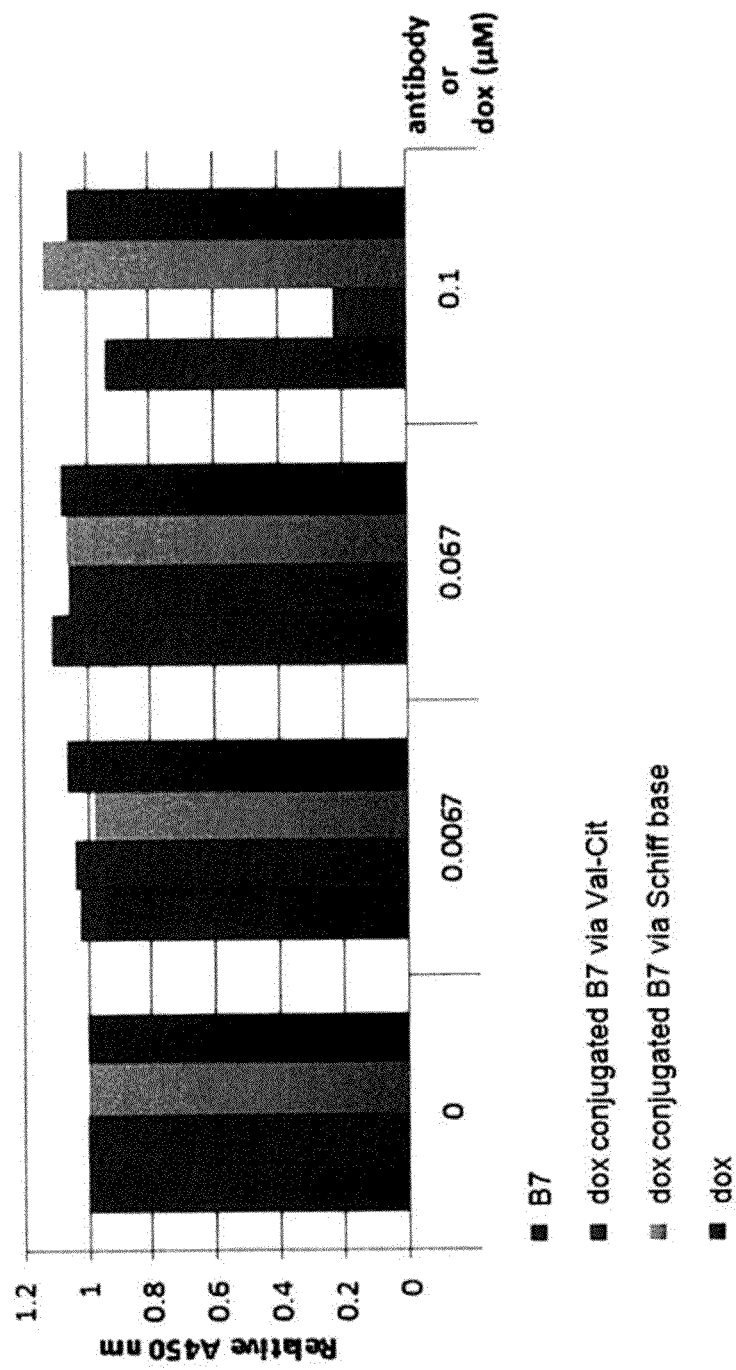
FIG. 18 shows the results of a cell proliferation assay for doxorubicin-conjugated B7 antibodies.

The pharmaceutical composition of the present invention has an advantage in that it can treat cancer at a cytotoxic drug concentration lower than the concentration of conventional cytotoxic drugs, making it possible to reduce the occurrence of side effects caused by injection of an excessive amount of the drug. According to one embodiment of the present invention, it was found that doxorubicin conjugated to a modified B7 antibody according to the present invention selectively inhibited the growth of A549 cells at a concentration lower than the concentration at which conventional doxorubicin exhibits cytotoxic effects (FIG. 18). This result supports that a composition for treating cancer comprising the antibody-drug conjugate of the present invention is effective for the treatment of cancer. Why cancer can be treated at a cytotoxic drug concentration lower than the concentration of conventional cytotoxic drugs is because the antibody comprising the cytotoxic drug conjugated thereto can deliver the drug specifically to cancer cells.

The pharmaceutical composition of the present invention for treating cancer may further comprise a pharmaceutically acceptable carrier and can be formulated with a carrier.

As used herein, the term "pharmaceutically acceptable carrier" refers to a carrier or a diluent that does not cause significant irritation to an organism and does not abrogate the biological activity and properties of the administered compound. Examples of a pharmaceutically acceptable carrier that may be used in a composition that is formulated into a liquid solution include saline, sterile water, Ringer's solution, buffered saline, albumin injectable solution, dextrose solution, maltodextrin solution, glycerol, ethanol, and a mixture of two or more thereof. If necessary, other conventional additives may be added, such as antioxidants, buffers and bacteriostatic agents. In addition, a diluent, a dispersant, a surfactant, a binder and a surfactant may be added to formulate the composition into injectable formulations, such as aqueous solutions, suspensions or emulsions, pills, capsules, granules or tablets.

The pharmaceutical composition of the present invention may be provided as any formulation comprising it as an active ingredient and can be prepared as an oral or parenteral formulation. Oral formulations comprising the composition of the present invention as an active ingredient include, for example, tablets, troches, lozenges, aqueous or oily suspensions, prepared powders or granules, emulsions, hard or soft capsules, syrups or elixirs. Tablet or capsule formulations may include a binder such as lactose, saccharose, sorbitol, mannitol, starch, amylopectin, cellulose or gelatin, an excipient such as dicalcium phosphate, a disintegrant such as maize starch or sweet potato starch, and a lubricant such as magnesium stearate, calcium stearate, sodium stearyl fumarate or polyethylene glycol wax. A capsule formulation may include, in addition to the above-mentioned substances, a liquid carrier such as fat oil.

Parenteral formulations comprising the composition of the present invention as an active ingredient include injectable formulations for subcutaneous injection, intravenous injection or intramuscular injection. To prepare an injectable formulation, the composition of the present invention may be mixed with a stabilizer or a buffer in water to prepare a solution or suspension, which may then be formulated in a unit dosage form such as an ampoule or a vial.

In still another aspect, the present invention, the present invention provides a method for treating cancer, which comprises administering the above-described antibody-drug conjugate or pharmaceutical composition to a subject.

Herein, the antibody-drug conjugate, the pharmaceutical composition and the cancer are as described above.

As used herein, the term "administering" means introducing the pharmaceutical composition of the present invention into a patient by any suitable method. The composition of the present invention may be administered by various oral or parenteral routes, as long as it can reach a desired tissue. Specifically, the composition of the present invention may be administered in a conventional manner by an oral, rectal, local, intravenous, intraperitoneal, intramuscular, intraarterial, transdermal, intranasal, inhalation, intraocular or intradermal route. Preferably, the composition is administered topically to cancer tissue.

As used herein, the term "subject" refers to any subject that can be treated with the antibody-drug conjugate or pharmaceutical composition of the present invention. Examples of the subject include, but are not limited to, humans and primates, as well as livestock such as cattle, pigs, sheep, horses, dogs and cats. Preferably, the subject may be a human being.

The method for treating cancer according to the present invention comprises a pharmaceutically effective amount of the antibody-drug conjugate or composition of the present invention. It will be obvious to those skilled in the art that the preferred total daily dose of the composition can be determined through reasonable medical judgment by the attending physician. The specific therapeutically effective dose of the composition for any particular patient may vary depending on various factors well known in the medical field, including the kind and degree of response to be achieved, concrete compositions according to whether other agents are used therewith or not, the patient's age, body weight, health condition, sex and diet, the time and route of administration, the secretion rate of the composition, the duration of treatment, other drugs used in combination or coincident with the composition of the present invention, and other factors known in the medical field. Thus, the effective amount of the composition for treating or preventing cancer, which is suitable for the purpose of the present invention, is preferably determined in view of the above-described particulars. In some cases, the anticancer composition of the present invention may be administered in combination with a known anticancer drug to increase the anticancer effect.

In still another aspect, the present invention provides the use of the antibody-drug conjugate for treating cancer.

Herein, the antibody-drug conjugate and the cancer are as described above.

MODE FOR INVENTION

Hereinafter, the present invention will be described in further detail with reference to examples. It is to be understood, however, that these examples are for illustrative purposes only and are not intended to limit the scope of the present invention.

Example 1

Production of c-Met-Specific Human B7 Antibody

Example 1-1

Preparation of Library Phage $2.7 \times 10^{10}$ human scFv library cells having diversity were cultured at 37° C. for 2-3 hours in a medium (3 L) containing 2×YT CM [tryptone (CONDA, 1612.00) 17 g, yeast extract (CONDA, 1702.00) 10 g, NaCl (Sigma, S7653-5 kg) 5 g, chloramphenicol (Sigma, C0857) 34 μg/ml)], 2% glucose (Sigma, G5400) and 5 mM MgCl$_2$ (Sigma, M2393) (OD600=0.5~0.7). Then, the cells were transfected with a helper phage and cultured in 2×YTCMK [2×YT CM, kanamycin (Sigma, K1876) 70 μg/ml, 1 mM IPTG (ELPISBIO, IPTG025)] medium at 30° C. for 16 hours. The cultured cells were centrifuged (4500 rpm, 15 min, 4° C.), and then 4% PEG (Fluka, 81253) 6000 and 3% NaCl (Sigma, 57653) were added to and dissolved in the supernatant and allowed to react on ice for 1 hour. The reaction solution was centrifuged (8000 rpm, 20 min, t), and the pellets were suspended in PBS, followed by centrifugation (12000 rpm, 10 min, 4° C.), thereby preparing a library phage.

Example 1-2

Panning Process

30 μg of purified c-Met (extracellular domain)-Fc was added to and dissolved in 4 ml of coating buffer [Na$_2$CO$_3$ (Sigma, S7795) 1.59 g, NaHCO$_3$ (Sigma, 58875) 2.93 g, NaN$_3$ (Sigma, 52002) 0.2 g], and the solution was placed in an immunosorb tube (Nunc 470319) which was then maintained in a rotator at 4° C. for 16 hours to coat c-Met on the wall of the tube. Then, the coated c-Met was blocked using 4% skim milk (BD, 232100) in PBS.

To the coated immunosorb tube, 2 ml of the library phage prepared in Example 1-1 was added and allowed to react at room temperature for 2 hours, and then the tube was washed five times with PBST (0.05%) and twice with PBS. After washing, specifically bound scFv-phages were eluted with 100 mM TEA (Sigma T-0886), and the eluted phages were transfected into *E. coli* (XL1-Blue, Stratagene, 200249) and amplified. The amplified phages were washed five times in first panning, 13 times in second panning and 23 times in third panning (Table 1).

TABLE 1

Comparison of antibody titer between panning stages

| Number of pannings | Number of phages introduced | Number of phages bound | Number of washings | Amount of antigen |
|---|---|---|---|---|
| 1 | $4.0 \times 10^{13}$ | $4.5 \times 10^7 / 2.7 \times 10^7 / 3.9 \times 10^7$ | 5 | 30 μg |
| 2 | $6.0 \times 10^{13}$ | $7.5 \times 10^6$ | 13 | 30 μg |
| 3 | $6.0 \times 10^{13}$ | $6.0 \times 10^9$ | 23 | 30 μg |

Table 1 above shows a comparison of the antibody titer according to panning stage. As can be seen in Table 1, the antibody titer increased as the number of pannings increased.

Example 1-3

Phage Antibody Screening by Phage ELISA

The cell stock, panned 1-3 times and thawed, was added to 5 ml of primary medium (2×YTCM, 2% Glucose, 5 mM MgCl2) to OD600=0.1, and then incubated at 37° C. for 2-3 hours (OD600=0.5-0.7). Then, the cells were transfected with M1 helper phage and cultured in secondary medium (2×YTCMK, 5 mM MgCl2, 1 mM IPTG) at 30° C. for 16 hours. The incubated cells were centrifuged (4500 rpm, 15 min, 4° C.), and the supernatant (panned poly scFv-phage) was transferred into a fresh tube. Each well of a 96-well immunoplate (NUNC 439454) was coated with 100 mg of antigen by treatment with coating buffer at 4° C. for about 16 hours, and then each well was blocked skim milk (4%) in PBS. Each well was washed with 0.2 ml of PBS-tween20 (0.05%), and 100 μl of each of 0, 5, 25, 125, 625 and 3125-fold dilutions of the panned poly scFV-phage was added to each well and allowed to react at room temperature for 2 hours. Next, each well was washed 4 times with 0.2 ml of PBS-tween 20 (0.05%), and then allowed to react with a 1:2000 dilution of secondary antibody anti-M13-HRP (Amersham 27-9421-01) at room temperature for 1 hour.

After washing with 0.2 ml of PBS-tween 20 (0.05%), 100 µl of a substrate solution of OPD tablet (Sigma 8787-TAB) in PC buffer [$C_6H_8O_7 \cdot H_2O$ (Sigma, C0706) 5.1 g, $Na_2HPO_4$ (Sigma, 57907) 7.3 g) was added to each well to develop color. After 10 minutes, the absorbance at 490 nm was measured (FIG. 1). FIG. 1 shows the results of ELISA for the c-Met polyclonal antibody. As can be seen in FIG. 1, the ability to bind to the antibody started to increase from the second polyclonal scFv-phage pool and reached a saturated state in the third pool.

Example 1-4

Selection of Monoclonal Antibody

A colony obtained from the polyclonal phage antibody group having high binding ability was cultured in a 96-well plate (Bioneer 90030) containing 1 ml of medium (2×YTCM, 2% glucose, 5 mM $MgCl_2$) at 37° C. for 16 hours. When the OD600 value reached 0.1, 100-200 µl of the cell culture was diluted in 1 ml of primary medium, and then incubated in a 96-deep well plate at 37° C. for 2-3 hours until the OD600 value reached 0.5-0.7. Next, the cells were transfected with M1 helper phage such that the MOI value was 1:20, after which the cells were incubated in secondary medium at 30° C. for 16 hours. The incubated cells were centrifuged (4500 rpm, 15 min, 4° C.), and the supernatant was added to 4% PEG 6000 and 3% NaCl and allowed to react on ice for 1 hour. Next, the reaction solution was centrifuged (8000 rpm, 20 min, 4° C.), and then the pellets were added to and dissolved in PBS, followed by centrifugation (12000 rpm, 10 min, 4° C.). The supernatant was transferred into a fresh tube and stored at 4° C. Next, each well of a 96-well plate was coated with 100 ng of antigen at 4° C. for 16 hours, and then each well was blocked with skim milk (4%) in PBS. Each well was washed with 0.2 ml of PBS-tween 20 (0.05%), and then 100 µl of the monoclonal phage (each 100 scFv-phage) obtained as described above was added to each well and allowed to react at room temperature for 2 hours. Next, each well was washed four times with 0.2 ml of PBS-tween 20 (0.05%), and then allowed to react with a 1/2000 dilution of anti-M13-HRP secondary antibody for 1 hour. Then, each well was washed with 0.2 ml of PBS-tween 20 (0.05%), after which color development was performed and the absorbance at 490 nm was measured (Table 2).

As can be seen in Table 2, 23 mono phage clones having a binding ability of 1 or higher to the antigen could be selected.

Example 1-5

Examination of Monoclonal Phages by Fingerprinting

1 µl of the primarily selected 16 monoclones for c-Met-Fc, 0.2 µl of Taq.DNA polymerase (Gendocs, 5 U/µl), 0.2 µl of each of 50 p/µl forward primer (pYG100-F) and reverse primer (pYG100-R), 0.6 µl of 10× buffer, 0.6 µl of 10 mM dNTP mix and 24.8 µl of distilled water were mixed with each other and subjected to colony PCR (iCycler iQ, BIO-RAD) under the following conditions: 1 cycle of 95° C. for 5 min, 34 cycles of 95° C. at 20 sec, 48° C. at 40 sec and 72° C. at 1 min, and 1 cycle of 72° C. at 5 min.

pYG100-F:
(SEQ ID NO: 17)
5'-cagctatgaccatgattacg-3' pYG100-R:
(SEQ ID NO: 18)
5'-cttattagcgtttgccatct-3'

The colony PCR product was analyzed on 1% agarose gel (Seakem LE, CAMERES 50004), and 0.2 µl of BstNI (Roche11288075001, 10 U/µl) was added thereto and allowed to react at 37° C. for 2-3 hours. The reaction was performed using 3 µl of 10× buffer, 10 µl of the PCR product, 0.2 µl of BstNI (10 U/µl) and 16.8 µl of distilled water.

The diversity of the digested products was analyzed on DNA polyacrylamide gel (30% acrylamide (Bio-RAD, 161-0156) 2.66 ml, 10×TBE 1 ml, $dH_2O$ 6.27 ml, 10% APS (sigma, A3678) 70 µl, TEMED (Bio-RAD, 161-0801) 7 µl) by monoclonal phage antibody fragments digested by BstNI (FIG. 2). FIG. 2 is electrophoresis photographs showing the results of fingerprinting for the c-Met monoclonal phages.

As can be seen in FIG. 2, diversity was observed for the monoclonal phage antibodies digested by BstNI, and 15 kinds of different antibodies were screened.

TABLE 2

Mono Phage ELISA for C-met-Fc

| | C-met (100 ng/well) | | | | | | | | anti-myc (100 ng/well) | | | | | | | FC | | |
|---|---|---|---|---|---|---|---|---|---|---|---|---|---|---|---|---|---|---|
| 2 ※ mono clone | | | | | | | | | | | | | | | | | | |
| A | 0.156 | 0.812 | 0.057 | 1.627 | 1.654 | 0.807 | 0.869 | 2.577 | 0.052 | 2.686 | 2.583 | 2.613 | 0.290 | 0.224 | 0.076 | 0.591 | 0.119 | 0.176 |
| B | 0.089 | 1.359 | 0.067 | 0.957 | 0.291 | 0.087 | 0.998 | 2.625 | 0.827 | 2.565 | 2.551 | 1.232 | 0.201 | 0.351 | 0.084 | 0.204 | 0.160 | 0.118 |
| C | 0.092 | 1.770 | 0.070 | 0.045 | 0.680 | 1.330 | 1.359 | 2.624 | 2.136 | 0.062 | 2.614 | 2.584 | 0.118 | 0.519 | 0.150 | 0.079 | 0.133 | 0.106 |
| D | 1.414 | 0.112 | 0.127 | 2.470 | 0.754 | 1.297 | 2.508 | 2.485 | 2.259 | 2.570 | 2.526 | 2.577 | 0.194 | 0.260 | 0.446 | 2.024 | 0.123 | 0.119 |
| E | 1.825 | 0.785 | 0.147 | 0.081 | 0.841 | 0.052 | 1.522 | 2.705 | 2.351 | 2.525 | 2.605 | 0.057 | 0.722 | 1.020 | 0.113 | 0.230 | 0.122 | 0.126 |
| F | 0.427 | 1.721 | 0.058 | 2.621 | 2.682 | 1.206 | 2.491 | 2.687 | 0.688 | 2.567 | 2.609 | 2.668 | 0.178 | 0.541 | 0.090 | 2.196 | 2.150 | 0.453 |
| G | 2.180 | 3.386 | 0.064 | 0.201 | 0.689 | 0.594 | 2.581 | 2.628 | 0.393 | 2.626 | 2.523 | 2.695 | 0.504 | 2.577 | 0.221 | 0.192 | 0.116 | 0.158 |
| H | 2.805 | 2.789 | 2.666 | 1.182 | 0.086 | 2.673 | 2.548 | 2.782 | 2.626 | 2.609 | 2.135 | 2.744 | 2.537 | 1.661 | 2.370 | 0.218 | 0.227 | 2.490 |
| 3 ※ mono clone | | | | | | | | | | | | | | | | | | |
| A | 2.899 | 2.807 | 2.807 | 0.082 | 2.752 | 2.670 | 2.621 | 2.605 | 2.704 | 0.065 | 2.736 | 2.701 | 2.381 | 1.920 | 2.384 | 0.148 | 2.544 | 2.463 |
| B | 2.890 | 2.742 | 2.755 | 0.062 | 2.729 | 2.618 | 2.564 | 2.624 | 2.683 | 0.061 | 2.590 | 1.917 | 0.148 | 2.452 | 2.505 | 0.083 | 0.198 | 1.801 |
| C | 2.835 | 0.063 | 2.753 | 2.747 | 2.681 | 2.714 | 2.543 | 0.053 | 2.689 | 2.692 | 2.666 | 2.222 | 2.008 | 0.122 | 2.518 | 2.490 | 2.563 | 2.485 |
| D | 2.861 | 0.052 | 2.588 | 2.677 | 0.061 | 1.026 | 2.607 | 0.054 | 1.846 | 2.062 | 0.062 | 2.624 | 2.474 | 0.124 | 1.360 | 2.387 | 0.142 | 0.190 |
| E | 0.488 | 0.060 | 2.797 | 1.998 | 2.678 | 2.755 | 2.521 | 0.334 | 2.640 | 0.414 | 2.636 | 2.544 | 0.122 | 0.155 | 2.485 | 0.100 | 2.467 | 0.236 |
| F | 0.066 | 0.059 | 2.761 | 2.833 | 2.719 | 2.754 | 0.125 | 0.054 | 2.564 | 2.662 | 2.620 | 2.585 | 0.112 | 0.129 | 0.154 | 2.184 | 2.554 | 2.546 |
| G | 0.066 | 2.826 | 0.075 | 2.862 | 2.656 | 2.515 | 0.059 | 2.645 | 0.054 | 2.641 | 2.582 | 1.784 | 0.100 | 2.494 | 0.233 | 2.501 | 2.557 | 1.194 |
| H | 2.923 | 2.821 | 2.776 | 0.291 | 2.545 | 2.743 | 2.535 | 2.665 | 2.593 | 0.091 | 1.360 | 1.936 | 2.533 | 1.315 | 2.519 | 0.278 | 2.124 | 2.596 |

Example 1-6

Examination of Monoclonal Phages by Sequencing 15 kinds of monoclonal phage clones for c-Met-Fc were inoculated in 5 ml of medium (2×YTCM, 2% glucose, 5 mM MgCl$_2$) and incubated at 37° C. for 16 hours. From the incubated monoclonal clones, DNAs were collected using a DNA purification kit (Nuclogen 5112), and the sequences thereof were analyzed (Solgent, Korea) (Table 3).

TABLE 3

Overview of C-met-Fc specific & selected scFv clones

| clone name | VH | Identities | VL | Identities | VH(CDR-a.a seq) | Vk(CDR-a.a seq) | C-Met | anti-myc | Fc | Group |
|---|---|---|---|---|---|---|---|---|---|---|
| A5 | VH3-53 | 93.0(266/286) | V2-13 | 93.8(270/288) | DVPEAGKGEFDY | NSRDRDDNHWV | 1.654 | 2.583 | 0.119 | 1 |
| B2 | VH3-53 | 89.0(260/292) | V1-3 | 96.3(284/295) | DDFYNGTLDF | SSYAGSYTSV | 1.359 | 2.625 | 0.351 | 2 |
| B7 | VH3-34 | 89.7(261/291) | V1-4 | 89.7(260/290) | FYGDYPSSYGMDV | SSYTDNRGLVL | 2.89 | 2.564 | 0.148 | 3 |
| D1 | VH3-53 | 96.2(275/286) | V1-4 | 97.3(286/294) | GHGKTDLDS | SSYTSSSTLA | 1.414 | 2.508 | 0.194 | 4 |
| C2 | VH3-23 | 91.9(271/295) | V1-13 | 94.9(278/293) | DLGRES RRWVYYFDL | QSYDSSLRSVV | 1.77 | 2.624 | 0.519 | 5 |
| D12 | VH3-49 | 98.3(288/293) | A27 | 97.5(272/279) | SKPVDDDYVLHYSAMEV | QQYGSSPLT | 1.026 | 2.624 | 0.19 | 6 |
| F2 | VH3-23 | 88.8(262/295) | O12 | 89.8(254/283) | DSAGGTLDV | QESDRALYI | 1.721 | 2.687 | 0.541 | 7 |
| F6 | VH3-23 | 95.9(282/294) | O12 | 95.2(257/270) | GRDLR | QQYDMYPVT | 1.206 | 2.668 | 0.453 | 8 |
| D6 | VH3-23 | 95.2(278/292) | L11 | 95.1(270/284) | GPKWEPHAFDV | QQTYDSPLT | 1.297 | 2.577 | 0.119 | 9 |
| E1 | VH3-23 | 93.9(276/294) | L5 | 94.0(267/284) | ADVMAARALDY | QQTDSUPLT | 1.825 | 1.522 | 0.722 | 10 |
| A10-2 | VH3-15 | 92.7(278/300) | L8 | 93.0(266/286) | G--RSAKRIAFDL | QQTYSFPRT | 0.919 | 1.902 | 0.410 | 11 |
| C9-2 | VH3-23 | 95.2(279/293) | V1-13 | 90.8(265/292) | NYDASRTWNHIDS | QSYASSLSGYV | 0.962 | 1.186 | 0.134 | 12 |
| E1-2 | VH3-23 | 91.4(266/291) | V1-13 | 92.8(271/292) | WARNYGMDV | QSYDSSLSGYV | 1.106 | 1.736 | 0.317 | 13 |
| F8-1 | VH1-2 | 87.7(257/293) | VH1-8 | 92.2(273/296) | GEPTRGAFEI | vGTWDASLSTGL | 1.157 | 0.107 | 0.314 | 14 |
| G1-2 | VH3-15 | 98.7(296/300) | L5 | 97.2(278/286) | GGRMGSP | QQANS-FPLT | 0.814 | 1.700 | 0.282 | 15 |

As can be seen in Table 3 above, the VH, VL and CDR regions of the selected antibodies were confirmed, the amino acid sequences of CDR3 in the heavy chain and light chain of the antibodies were analyzed and had different sequences.

Example 1-7

Analysis of Whole IgG Conversion

In order to convert monoclonal phage antibodies against c-Met from phage to whole IgG vector, 1 µl of heavy chain monoclonal DNA, 10 pmole/µl of each of the following heavy-chain forward primer (NATVH4-2) and heavy chain reverse primer (NATJH-ALL Nhe I), 5 µl of 10× buffer, 1 µl of 10 mM dNTP mix, 0.5 µl of pfu DNA polymerase (Solgent, 2.5 U/µl), and distilled water (iCycler iQ, BIO-RAD) were mixed to perform a colony PCR (iCycler iQ, BIO-RAD). The PCR is performed under the following conditions: 1 cycle of 95° C. at 2 min, 30 cycles of 95 for 20 sec, 55° C. for 40 sec and 72° C. 1 min, and 1 cycle of 72 for 5 min.

```
NATVH4-2:
                                      (SEQ ID NO: 19)
5'-TTGGTGGCCACAGCGGCCGATGTCCACTCGCAGGTGCAGC
TACAGCAGTG-3'

NATJH-ALL Nhe I:
                                      (SEQ ID NO: 20)
5'-GAGGAGGCTAGCTGAGGAGACGGTGA-3'
```

In addition, the light chain was also subjected to colony PCR in the same manner as above using the following light-chain forward primer (NATVL4) and reverse primer (NATJL2-R).

```
NATVL4:
                                      (SEQ ID NO: 21)
5'-TTGGTGGCCACAGCGGCCGATGTCCACTCGCAGTCTGCCC
TGACTCAGCC-3'

NATJL2-R:
                                      (SEQ ID NO: 22)
5'-GAGGAGAGATCTTAGGACGGTCAGCTTGGTCCC-3'
```

Figure 3A:
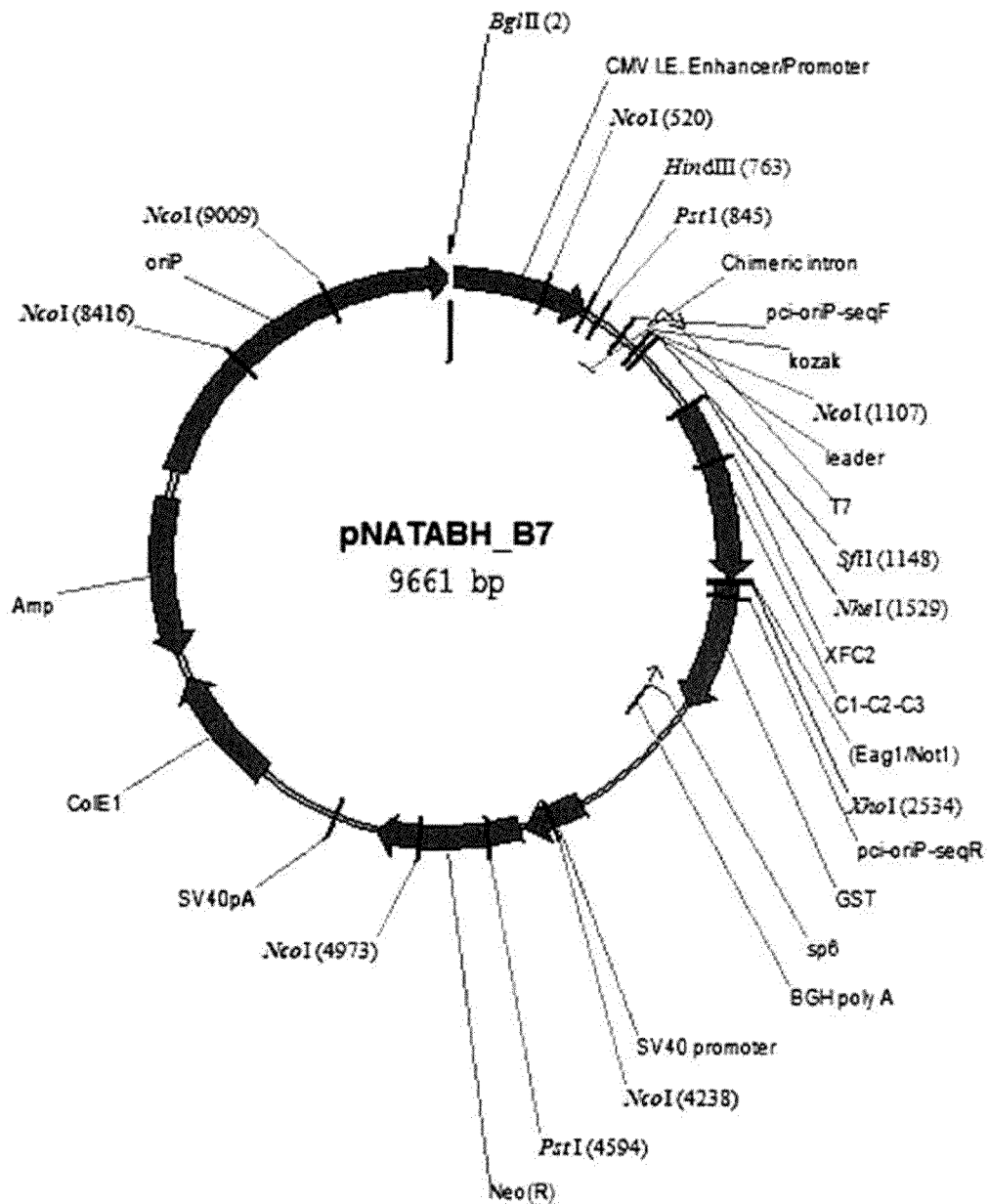
FIGS. 3a and b is a vector map showing the heavy-chain expression vector pNATABH_B7 and FIG. 3b is a vector map showing the light-chain expression vector pNATABL_B7.

The heavy chain gene obtained through PCR was purified with a DNA-gel extraction kit (Qiagen). 1 µl of pNATABH vector (10 ng), 15 µl of heavy chain (100-200 ng), 2 µl of 10× buffer, 1 µl of ligase (1 U/µl), and distilled water were mixed with the gene and the mixture was allowed to stand at room temperature for 1-2 hours for linkage to the vector, thereby constructing the heavy-chain expression vector pNATABH_B7 (FIG. 3a). FIG. 3a is a vector map showing the heavy-chain expression vector pNATABH_B7 (FIG. 3a). The vector was allowed to stand on ice for 30 minutes along with a cell for transformation (XL1-blue), followed by heat shock at 42° C. for 90 sec for transfection. It was again left to stand on ice for 5 minutes and 1 ml of LB medium was injected, followed by incubation at 37° C. for 1 hour. The mixture was inoculated in LB Amp liquid medium, followed by incubation at 37° C. for 16 hours. Single colony was inoculated into 5 Ml of LB Amp liquid medium, followed by incubation at 37° C. for 16 hours. A DNA-prep kit (Nuclogen) was used to extract DNA from the medium.

Figure 3B:
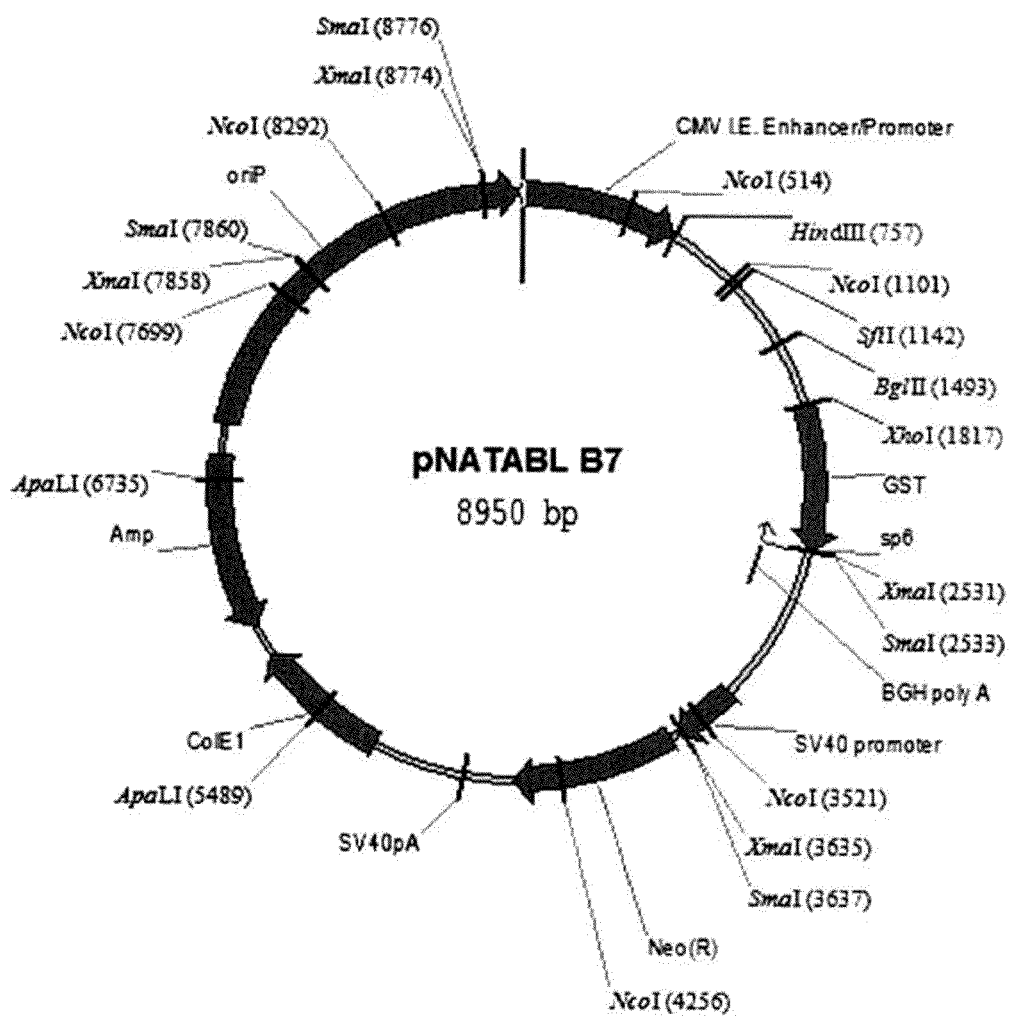

Meanwhile, the light-chain expression vector pNAT-ABL_B7 (FIG. 3b) was constructed in the same manner as above using the pNATABL vector and was used to extract light-chain DNA. FIG. 3b is a vector map showing the light-chain expression vector pNATABL_B7.

Sequencing of the obtained DNA was performed by using a CMV-proF primer (SEQ ID NO 23: AAA TGG GCG GTA GGC GTG) (Solgent). As a result, it was confirmed that the sequences of heavy and light chains of the 15 clone phages against c-Met-Fc converted into whole IgG were identical to those of the phage antibodies.

Example 1-8

Antibody Expression and Purification

PEI reagent and the heavy chain and light chain DNAs obtained by cloning the variable region of B7 phage into the pNATAB vector were mixed with serum-free DMEM medium, and 293E cells were treated with the mixture and cultured. When the 293E cells reached a confluence of about 70% in a 100 mm plate, 6 μg of each of the heavy-chain and light-chain DNAs and 20 μg of PEI (#23966, Polysciences, USA) were mixed, allowed to react at room temperature for 20 minutes, and then added to the cells. After 24 hours, the medium was replaced with serum-free DMEM medium, and then the medium was recovered and replaced with fresh medium at 2-day intervals. The recovered medium was subjected to Western blot analysis using secondary antibody (Goat Anti-human IgG, (Fc), Thermo, #31413) to examine antibody expression (FIG. 4). FIG. 4 is a photograph showing the results of Western blot analysis performed to examine whether the antibody was expressed. In FIG. 4, "non-reducing" indicates the results of Western blot analysis performed in a non-reducing condition containing no β-mercaptoethanol, and "reducing" indicates the results of Western blot analysis performed in a reducing condition containing β-mercaptoethanol, and $1^{st}$ to $4^{th}$ indicate the order of each sample obtained while replacing the medium at 48-hr intervals. As can be seen in FIG. 4, in the non-reducing condition, a molecular weight of about 240 kDa was shown, and in the reducing condition, the heavy chain and light chain of the antibody were separated to show an about 55-kDa heavy-chain portion detectable by the secondary antibody, suggesting that the antibody was properly prepared by the above preparation method.

Figure 5:
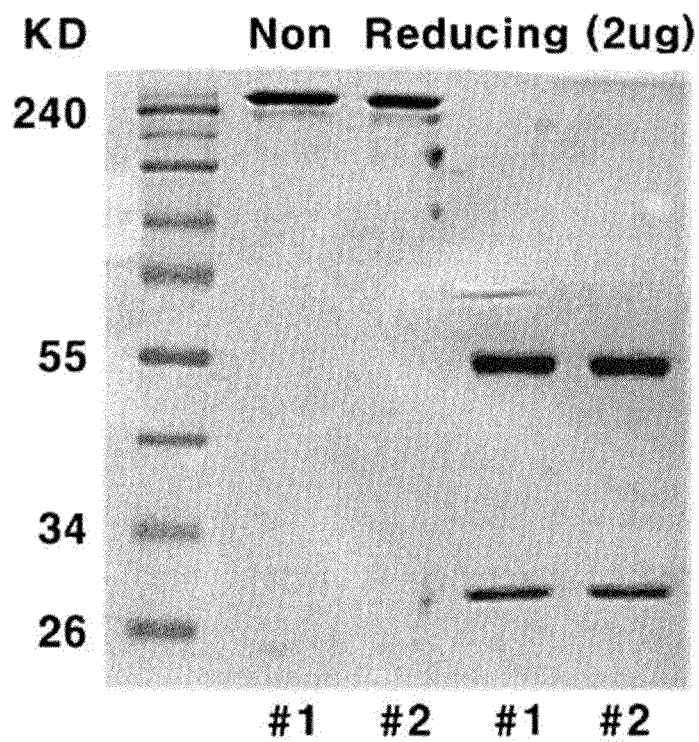
FIG. 5 is a photograph showing the results of electrophoresis of a purified antibody.

The medium confirmed to have the expressed antibody was centrifuged, and then filtered through a 0.22 μm filter (#PR02890 Millipore, USA). A 10 ml column was packed with 400 μl of Protein A Bead (#17-1279-03 GE, Sweden) and washed with PBS, and then about 50 ml of the medium having the expressed C-Met B7 antibody was allowed to pass through the column. The medium was introduced at a flow rate of 0.8 ml/min using a Peri-start pump (Bio-rad, EP-1 Econo-pump). When the medium completely passed through the column, the column was washed with about 100 ml of PBS, and the purified C-Met B7 antibody was recovered with 0.1 M glycine-HCl (#G7126, Sigma, USA). The recovered protein was pH-neutralized with 1M Tris pH 9.0 (#T-1503, Sigma, USA) and dialyzed using PBS, thereby purifying the antibody. The purified antibody was quantified with BCA solution (Thermo, #23228, #1859078) and subjected to SDS-PAGG in order to determine whether or not the antibody was properly purified, had a correct antibody structure and was properly quantified (FIG. 5). FIG. 5 is a photograph showing the results of electrophoresis of the purified antibody. In FIG. 5, "Non" indicates the results of electrophoresis performed in a non-reducing condition containing no β-mercaptoethanol, and "Reducing" indicates the results of electrophoresis performed in a reducing condition containing β-mercaptoethanol, and Reducing indicates, and #1 and #2 indicates the antibodies that resulted from the two purification experiments, respectively. As can be seen in FIG. 5, in the non-reducing condition, a molecular weight of about 240 kDa was shown, and in the reducing condition, the antibody was separated into an about 55 kDa heavy-chain portion and an about 26 kDa light-chain portion, suggesting that the antibody was properly purified by the above purification method.

Example 2

Production of B7 c-Met Antibody Comprising Extra Cysteine (Extra Cys) (Modification of B7)

2-1: Production of Antibody

Figure 8:
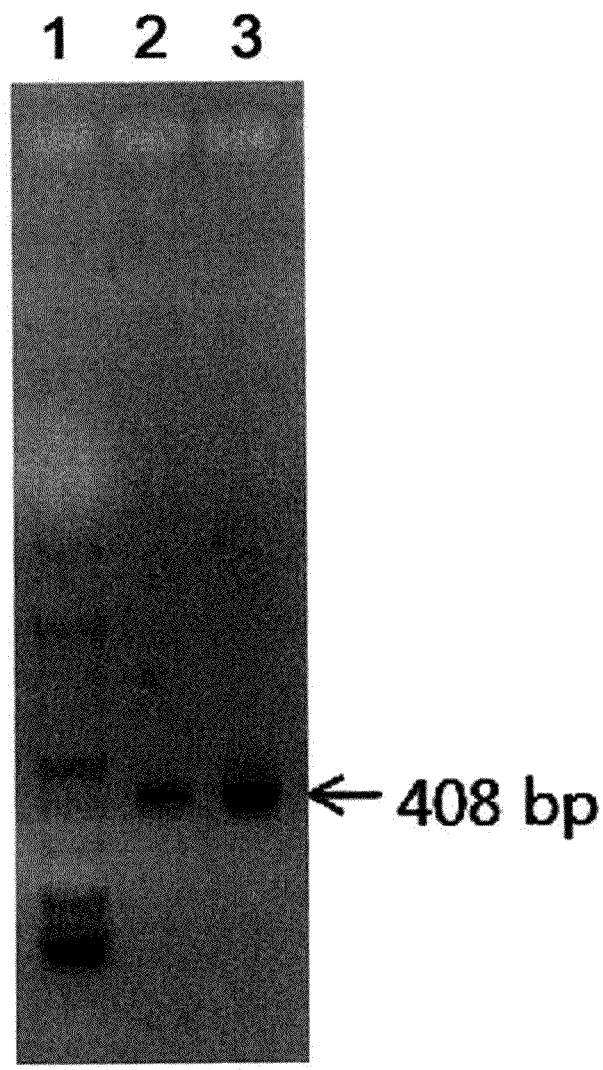
FIG. 8 shows the results of PCR of insert DNA used for cloning of modified B7 antibody.

In order to conjugate a cytotoxic drug to the c-Met-targeting B7 antibody produced in Example 1, an antibody comprising extra Cys was constructed. A plasmid expressing the heavy chain of B7 was used as a template, and primers comprising the Cys codon TGC were synthesized. 250 μM dNTP mixture, 1 μM forward primer (SEQ ID NO: 24), 1 μM reverse primer (SEQ ID NO: 25) and 1 unit of DNA taq polymerase (Enzynomics) were mixed with each other to make PCR buffer and subjected to PCR under the following conditions, thereby preparing an insert DNA fragment (FIG. 8): heating at 95° C. for 5 min, and then 30 cycles of 95° C. for 30 sec, 50° C. for 30 sec and 72° C. for 30 sec, followed by 72° C. for 7 min and 30 sec. The obtained DNA was purified using a PCR purification kit (Nucleogen).

The primers used in the PCR are as follows:

```
Forward primer:
                                        (SEQ ID NO: 24)
5'-TTGGTGGCCACAGCGGCCGATGTCCACTCGCAGGTACAGC
TACAGGAGTG-3';

Reverse primer:
                                        (SEQ ID NO: 25)
5'-GAGGAGGCTAGCGCATGAGGAGACGGTGA-3',
``` wherein the underlined sequence indicates the complementary codon of extra Cys.

Figure 9:
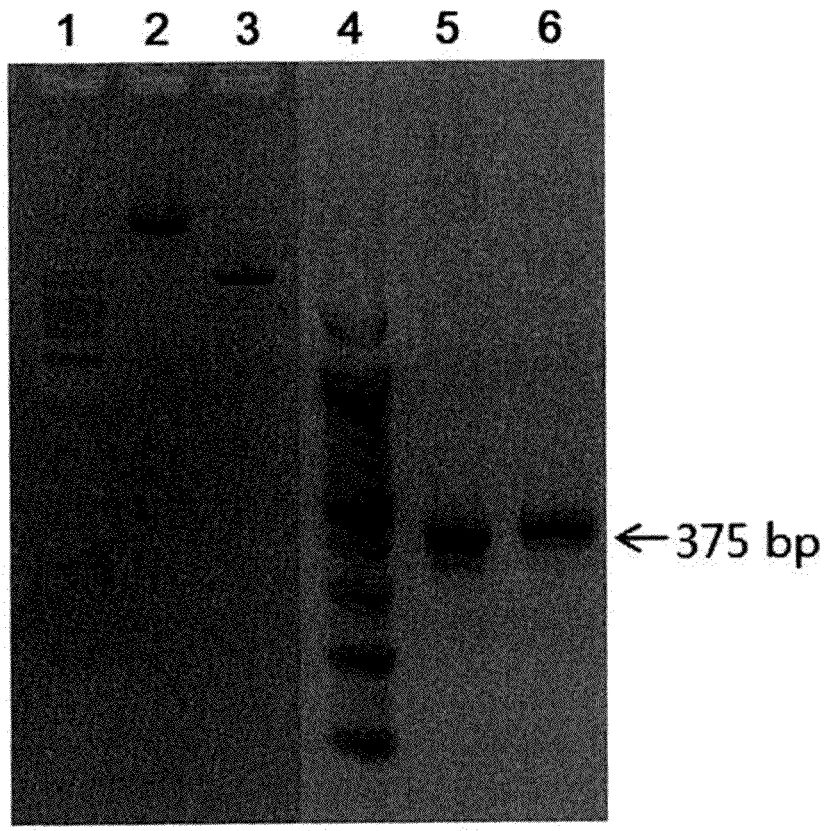
FIG. 9 shows the results of restriction enzyme cleavage of insert DNA used for cloning of modified B7 antibody.

About 1 μg of the insert DNA fragment and a pNATAB heavy-chain vector were reacted with 5 units of NheI (New England Biolab, #R0131) at 37° C. for 2 hours, and then 5 units of SfiI (New England Biolab, #R0123) was added thereto and allowed to react at 50° C. for 2 hours (FIG. 9). The resulting DNA was purified using a PCR purification kit (Nucleogen). In order to ligate the insert DNA, obtained by restriction enzyme cleavage, with a vector, 1 unit of T4 DNA ligase (Roche #481220) was added to a mixture of 50 ng of a vector and 6 ng of the insert DNA (vector:insert DNA=1:3 by molar ratio) and allowed to react overnight. 5 μl of the reaction mixture was mixed with 50 μl of DH5α competent cells and transformed into the cells by a heat shock method. The cells were grown on an ampicillin-containing LB agar plate, and the produced colonies were sequenced, after the resulting plasmid was purified.

The sequence of the cloned antibody was analyzed, and as a result, it was found that the light-chain variable region has a nucleic acid sequence set forth in SEQ ID NO: 12 and an amino acid sequence set forth in SEQ ID NO: 11; the light-chain constant region has a nucleic acid sequence set forth in SEQ ID NO: 16 and an amino acid sequence set forth in SEQ ID NO: 15; the heavy-chain variable region has a nucleic acid sequence set forth in SEQ ID NO: 10 and an amino acid sequence set forth in SEQ ID NO: 8; the CDR1, CDR2 and CDR3 of the heavy-chain variable region have the sequences set forth in SEQ ID NOS: 1, and 3, respectively; and the CDR1, CDR2 and CDR3 of the light-chain variable region have the sequences set forth in SEQ ID NOS: 4, 5 and 6, respectively.

2-2: Expression and Purification of Antibody

To express the modified B7 c-Met antibody cloned in Example 2-1, 293E cells were used. When 293E cells were grown to a confluence of about 70% on a 100 mm plate, 15 μg of each of heavy-chain and light-chain DNAs was mixed with 20 μg of PEI (#23966, Polysciences, USA), and the mixture was allowed to react at room temperature for 20 minutes, and was then added to the cells. After 24 hours, the medium was placed with serum-free DMEM medium, which was then recovered and replaced with fresh medium at 2-day intervals. The recovered medium was analyzed by Western blotting using secondary antibody (Goat Anti-human IgG, (Fc), Thermo, #31413) to measure the expression of the antibody.

The medium confirmed to have the expressed antibody was centrifuged, and then filtered through a 0.22 μm filter (#PR02890 Millipore, USA). A 10 ml column was packed with 400 μl of Protein A Bead (#17-1279-03 GE, Sweden) and washed with PBS, and then about 50 ml of the medium having the expressed modified B7 antibody was allowed to pass through the column. The medium was introduced at a flow rate of 0.8 ml/min using a Peri-start pump (Bio-rad, EP-1 Econo-pump). After the medium completely passed through the column, the column was washed with about 100 ml of PBS, and the purified modified B7 antibody was recovered with 0.1 M glycine-HCl (#G7126, Sigma, USA). The recovered protein was pH-neutralized with 1M Tris pH 9.0 (#T-1503, Sigma, USA) and dialyzed using PBS. The purified antibody was quantified with BCA solution (Thermo, #23228, #1859078) and subjected to SDS-PAGE in order to determine whether or not the antibody was properly purified, had a correct antibody structure and was properly quantified (FIG. 10).

Figure 10:
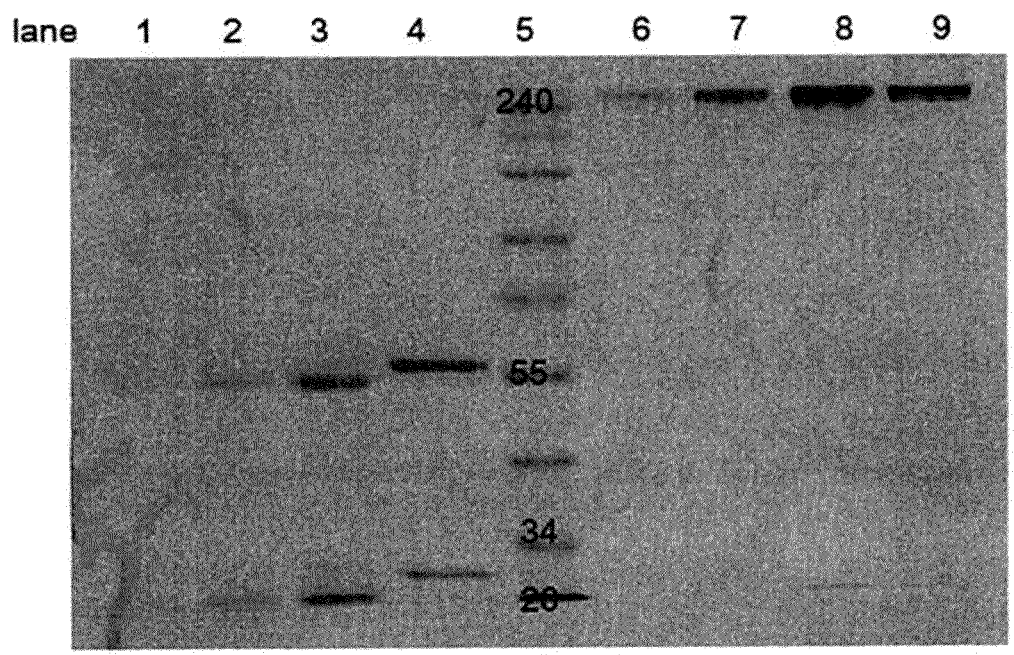
FIG. 10 shows the results of SDS-PAGE electrophoresis performed to confirm the purification of modified B7 antibody.

As can be seen in FIG. 10, it was shown by SDS-PAGE and Coomassie blue staining that the antibody was properly purified and was formed correctly in quantitative and structural terms.

Example 3

FACS Analysis

Whether the human modified B7 antibody according to the present invention easily binds specifically to c-Met was examined by FACS analysis. Each of A549 cells, known to readily express the c-Met receptor, and Cos-7 cells that overexpressed c-Met, was prepared, washed twice with PBS, detached by treatment with trypsin, washed again with PBS, and then suspended in PBS (PBA buffer) containing 1% BSA protein. Then, the cells were treated with the purified modified B7 antibody of Example 2 at 1:100 at 4° C. for 1 hour, after which the cells were washed with PBA buffer and precipitated by centrifugation at 8000 rpm for 1 minute. The washing and precipitation process was repeated three times. Then, the modified B7 antibody was treated for 20 minutes with a 1:100 dilution of secondary antibody (Invitrogen, Alexa Fluor 488 goat anti-human IgG, #A11013) that detects human antibody. The cells were washed in the same manner as described above and analyzed by FACS analyzer (BD Cantoll Flow Cytometer), and the results of the analysis are shown in FIG. 11.

As a result, it was found that the modified B7 antibody did bind specifically to c-Met while maintaining the property of the original B7 antibody that specifically recognizes c-Met (FIG. 11).

Example 4

Figure 12:
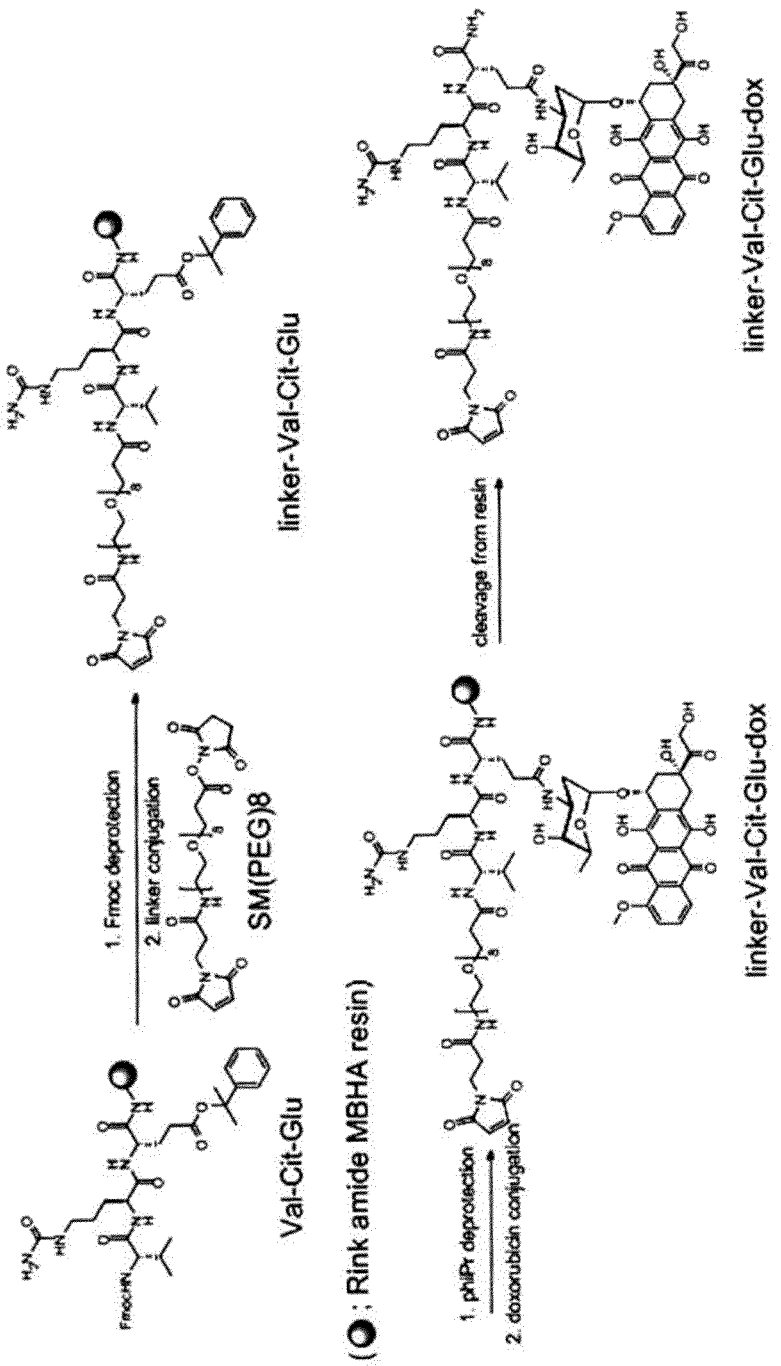
FIG. 12 schematically shows a process for synthesizing a doxorubicin derivative (linker-Val-Cit-Glu-dox).

Synthesis of Doxorubicin Derivative and Analysis of Release of Cytotoxic Drug by Enzyme In Vivo 50 mg of Rink amide MBHA resin (0.59 mmole/g) was added to a poly-prep chromatography column (Biorad, #731-1550) and swollen with each of 5 ml of methylene chloride and DMF for 5 minutes. 10 ml of a DMF solution containing 20% peridine was added to the resin, and the mixture was stirred with a rotational shaker at room temperature for 5 minutes (9 rpm) to deprotect the Fmoc group. The resin was washed with methylene chloride (10 ml, three times) and DMF (10 ml, twice), and a solution of FmocGlu(O-2-phiPr)OH (86.5 mg, 6 equiv), benzotriazole-1-yl-oxy-tris-pyrridino-phosphonium hexafluorophosphate (PyBOP, 92 mg, 6 equiv) and N,N-diisopropylethylamine (31 μl, 6 equiv) in 5 ml of DMF was added to the resin, which was then stirred at a constant speed (9 rpm) at room temperature for 1.5 hours. The resulting material was washed with methylene chloride and DMF in the same manner as described above and was tested with TNBS (2,4,6-trinitrobenzenesulfonic acid) to confirm completion of the reaction. Next, Fmoc deprotection and protected amino acid coupling were sequentially carried out, and Cit (citrulline) and Val (valine) were also sequentially coupled (FIG. 12; resin-linked Val-Cit-Glu).

Figure 13:
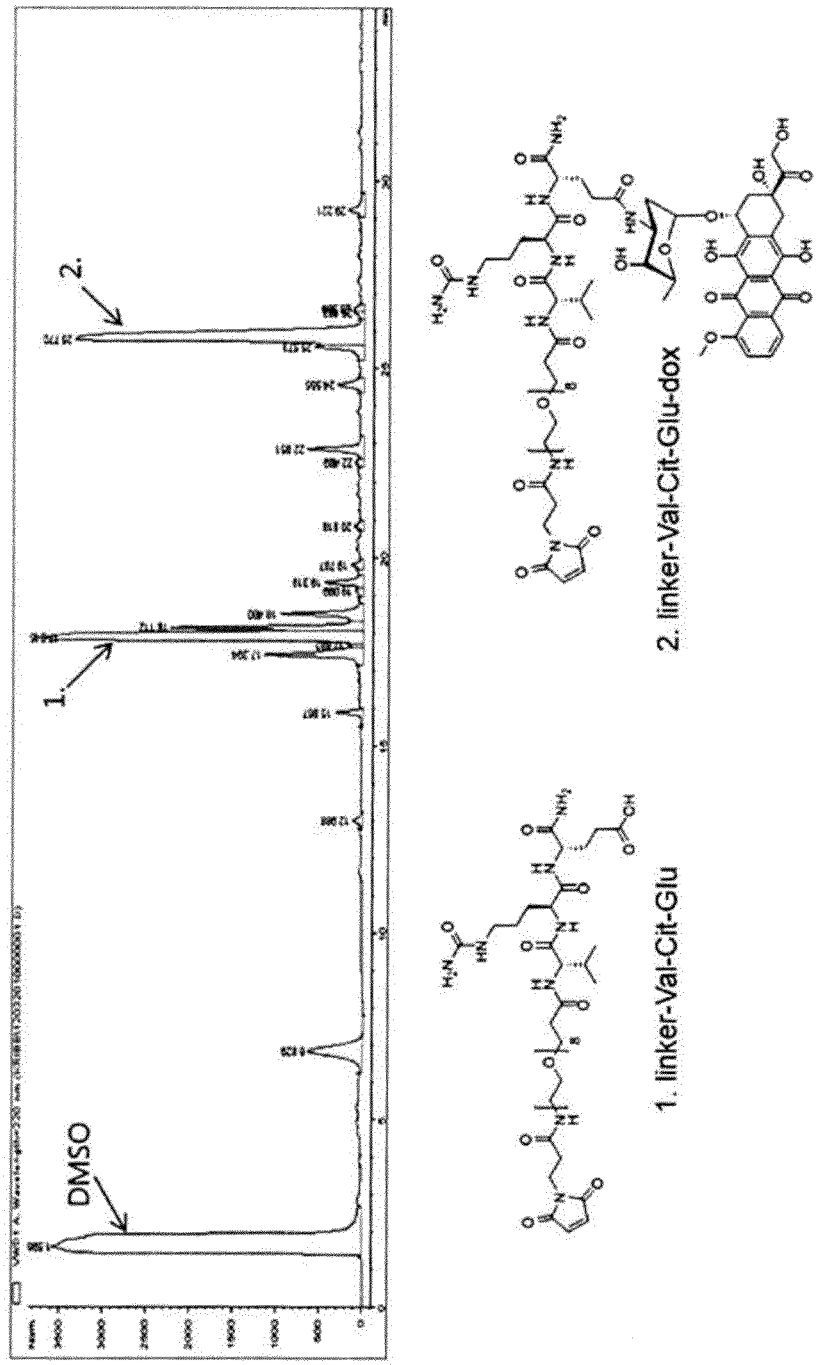
FIG. 13 shows the results of HPLC analysis of a doxorubicin derivative (linker-Val-Cit-Glu-dox).

After Fmoc deprotection of the final amino acid, 0.3 ml (1.5 equiv) of a DMSO solution containing 100 mg/ml of SM (PEG) 8 (Piearce, #22108) was added thereto, followed by stirring at room temperature for 2 hours. The reaction product was tested with TNBS to confirm completion of the reaction and washed, after which the phiPr group was deprotected in the following manner. 10 ml of methylene chloride containing 2% TFA (trifluoroacetic acid) was added to the reaction product, followed by stirring at room temperature for 3 hours. After washing, a solution of 96 μl of 10 mg/ml doxorubicin DMF solution (Sigma, #D1515), 1 mg of HOBt (hydroxybenzotriazole) and 3 mg of HCTU (2-(6-chloro-1H-benzotriazole-1-yl)-1,1,3,3-tetramethylaminium hexafluorophosphate) in 5 ml of DMF was added to the reaction product, followed by stirring at room temperature. The resulting material was washed with methylene chloride and DMF, and a solution of cleavage cocktail (TFA:TIS (triisopropylsilane):water (95:2.5:2.5)) was added thereto and stirred at room temperature, thereby separating a doxorubicin (dox)-conjugated peptide from the resin (FIG. 12; linker-Val-Cit-dox). Air was blown to the resulting peptide derivative mixture to remove TFA, and 1 ml of a solution of ice cold n-hexane: diethyl ether (1:1) was added to precipitate the peptide derivative mixture. The resulting material was centrifuged at 4° C. and 13000 rpm for 10 minutes to obtain a pellet. The pellet was dissolved in 300 μl of DMSO and separated by HPLC (Agilent 1100) (FIG. 13). As a stationary phase for separation, Zorbax C18 (5 μm, 4.6 mm×15 cm) was used, and a mobile phase, buffer A (0.1% TFA-containing $H_2O$) and buffer B (0.1% TFA-containing $CH_3CN$) were used. The concentration gradient conditions used are as follows: 5% buffer B for 5 minutes, and then linear increase from 5% to 60% at a rate of 1 ml/min for 35 minutes or more. The synthesized peptide derivative linker-Val-Cit-Glu was analyzed by MALDI-TOF mass spectrometry (Applied Biosystems) (FIG. 14). MS [M+H]+: 977.5 (calculated), 977.2 (observed). The peptide derivative linker-Val-Cit-Glu-dox had the absorbance at 495 nm of doxorubicin as a major substance produced in the synthesis process, even though doxorubicin was not detected by the MALDI-TOF mass spectrometer due to its property.

Example 5

Synthesis of Doxorubicin Derivative and Analysis of Release of Cytotoxic Drug by Acidity In Vivo (Modification of Doxorubicin-Conjugated Via Schiff Base)

55 mg of H-Phe-H-Novasyn TG resin (Novabiochem, #04-12-3712, 0.24 mmole/g) was added to a poly-prep chromatography column (Biorad, #731-1550) and swollen with 5 ml of each of methylene chloride and DMF for 5 minutes. 0.1 ml (1.1 equiv) of a DMSO solution containing 100 mg/10 of SM(PEG)8 (Piearce, #22108) was added thereto and stirred at room temperature for 1 hours. The resulting resin was washed once with 1 ml of TFA, and 1.5 ml of cleavage cocktail (acetic acid:water:dichloromethane:methanol=10:5:63:21) was added thereto and stirred at room temperature for 30 minutes, thereby separating an aldehyde linker from the resin (FIG. 15). The resulting resin was washed twice with methanol to collect the separated linker mixture, and the solvent was removed with air. 1 ml of a solution of ice cold n-hexane:diethyl ether (1:1) was added to precipitate the aldehyde linker mixture, which was then centrifuged at 4° C. and 13000 rpm for 10 minutes to obtain a pellet. The pellet was dissolved in 0.2 ml of water. 5 mg of doxorubicin was mixed with 0.1 ml of the aldehyde linker solution and stirred in 0.05M sodium phosphate buffer (pH 5.8) (1 ml final scale) overnight at room temperature. The resulting dox-linker mixture solution was used directly for conjugation to the modified B7 antibody without undergoing any separation process.

Example 6

Figure 6:
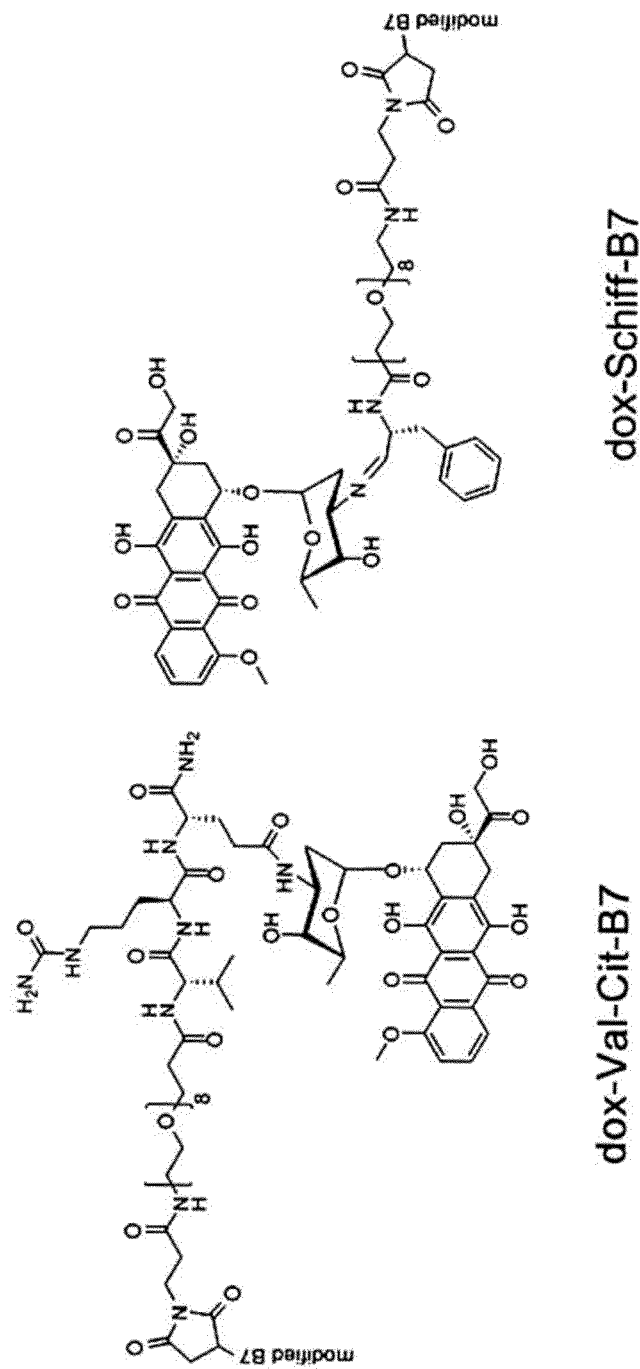
FIG. 6 schematically shows the structure of doxorubicin-conjugated B7 antibody.
Figure 7A:
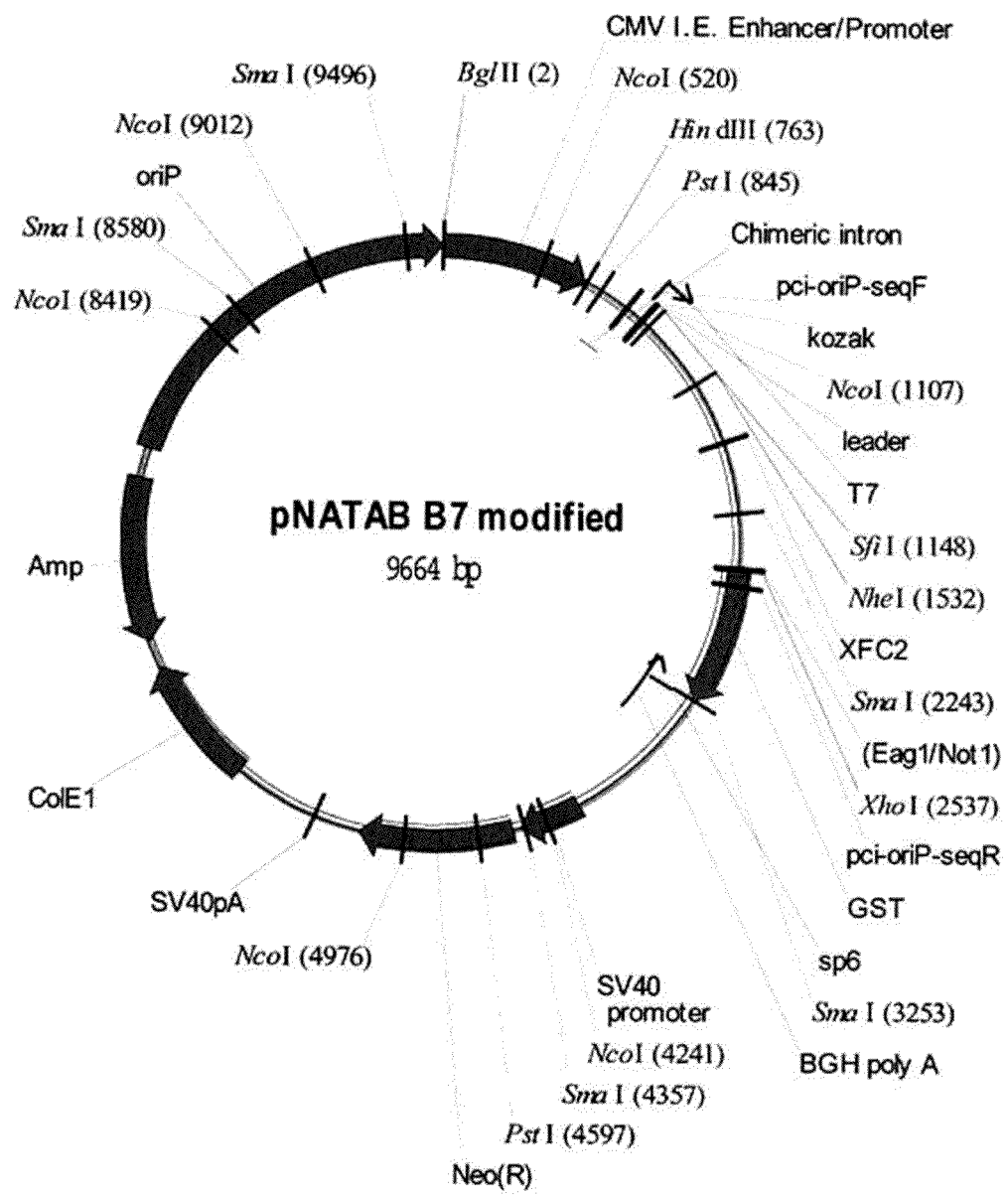
FIGS. 7a and 7b are maps of a vector for expression of the heavy-chain and light chain of modified B7 antibody.
Figure 7B:
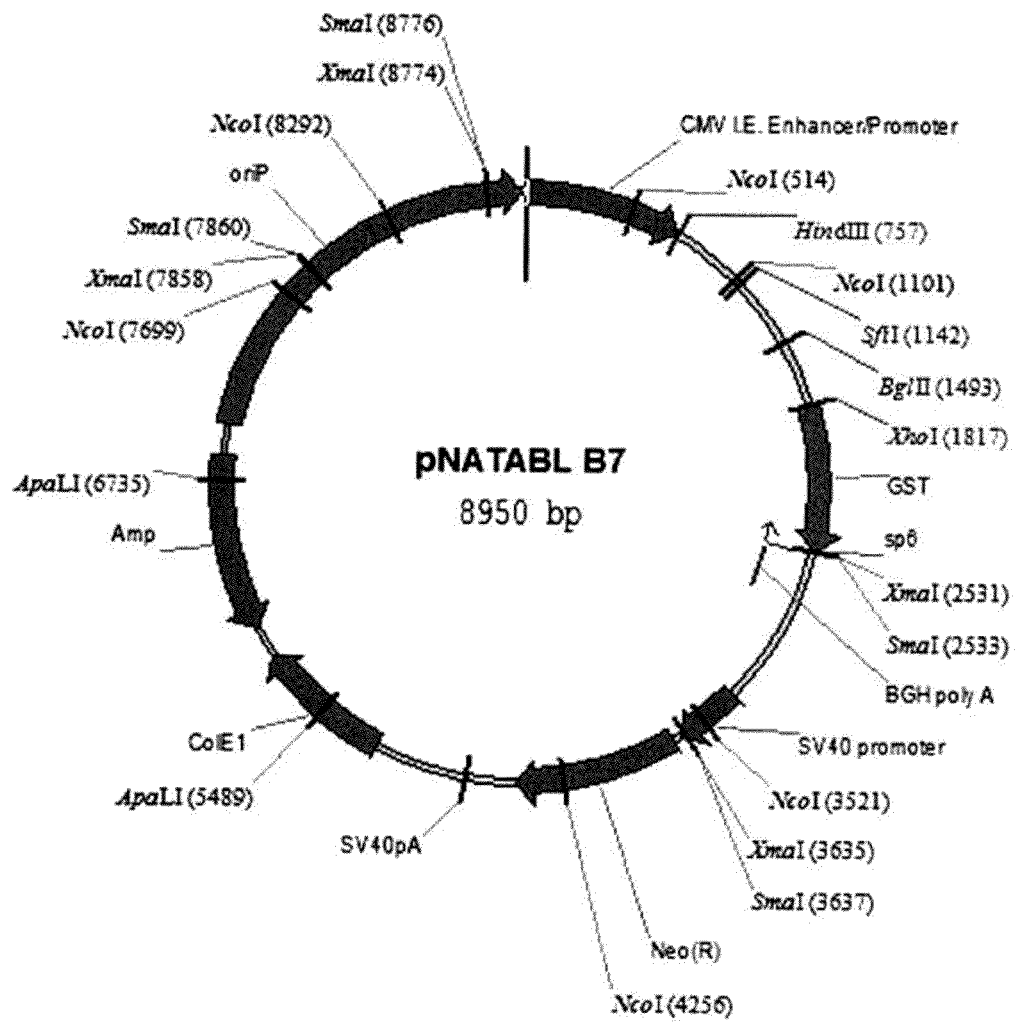

Conjugation of Doxorubicin to Modified B7 Antibody (FIG. 6)

Figure 16:
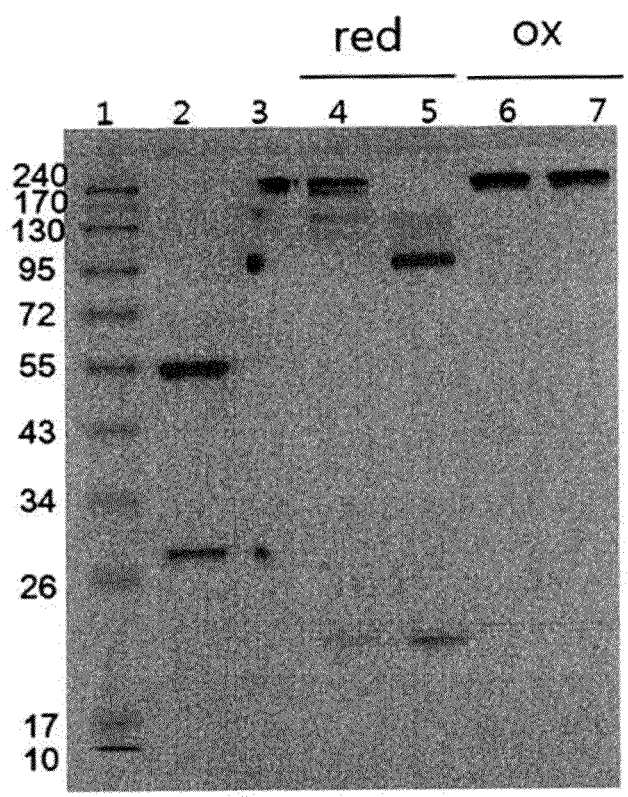
FIG. 16 shows a process of assembling modified B7 antibody by reduction and oxidation.

24 µl of 1 mM TCEP (tris(2-carboxyethyl)phosphine) was added to 50 µl of the modified B7 antibody (0.714 mg/ml PBS phosphate base saline) (0.2 ml final scale) and stirred at room temperature for 5 minutes so that extra Cys reduced portions of the disulfide bonds to sufficiently expose free thiol groups. The reaction product was desalted using a Zeba spin desalting columns (7K MWCO; Thermo, #89882), and 6.4 µl of 50 mM dhAA (dehydro-ascorbic acid) was added to the resulting reduced modified B7, which was then oxidized for 3 hours, thereby performing assembly of the antibody (FIG. 16). Then, the reaction product was desalted using a Zeba spin desalting column (7K MWCO; Thermo, #89882), and an excessive amount of linker-Val-Cit-Glu-dox or dox-linker solution in PBS buffer was added thereto and allowed to 4° C. for 2 hours. The resulting doxorubicin-conjugated B7 antibody was purified by a protein A column. The O.D. values of the resulting fractions at 280 nm and 495 nm were measured with NanoQuant (Tecan, infinite200) to determine whether doxorubicin was conjugated to the modified B7 antibody (FIG. 17).

As a result, it was found that doxorubicin was stably conjugated to the modified B7 antibody (FIG. 17).

Example 7

WST-1 Cell Proliferation Assay

In order to examine whether the doxorubicin-conjugated modified antibody has any effect on cell proliferation by binding to c-Met, a WST-1 assay (cell proliferation assay) was performed. Specifically, A549 cells grown on a 100 mm plate was detached by treatment with trypsin, and then seeded into each well of a 96-well plate at a density of 5000 cells/well. After one day, the medium was replaced with 3% serum-containing RPMI, and the cells were cultured for one day. Each well was treated with various concentrations of each of doxorubicin (dox) and the doxorubicin-conjugated modified B7 antibody (dox conjugated B7), and after 24 hours, each well was treated with 10 µl of WST-1 solution in a $CO_2$ incubator at 37° C. for 2 hours. Next, the O.D. value at 450 nm was measured with NanoQuant (Tecan, infinite 200).

As a result, as can be seen in FIG. 18, the results of measurement at 24 hours after treatment with the doxorubicin-conjugated modified B7 antibody indicated that the B7 antibody selectively inhibited the growth of the A549 cells at a concentration lower than the concentration at the cytotoxic effect of doxorubicin appeared. Thus, it can be seen that the doxorubicin-conjugated modified B7 antibody of the present invention binds to c-Met and selectively release doxorubicin into cells, thereby inhibiting the growth of the cells.

The above-described results suggest that the doxorubicin-conjugated modified B7 antibody of the present invention can be used as a therapeutic agent that acts specifically against cancer cells. Particularly, the results suggest that the doxorubicin-conjugated modified B7 antibody acts specifically against a hypoxic tumor difficult to treat with conventional drugs.

What is claimed is:

1. An antibody-drug conjugate comprising a cytotoxic, drug conjugated to a c-Met-specific human antibody, wherein the antibody comprises:
 a heavy-chain variable region comprising:
  i) a heavy-chain CDR1 comprising amino acids having the sequence set forth it SEQ ID NO: 1;
  ii) a heavy-chain CDR2 comprising amino acids having the sequence set forth in SEQ ID NO: 2; and
  iii) a heavy-chain CDR3 comprising amino acids having the sequence set forth SEQ ID NO: 3; and
 a light-chain variable region comprising:
  i) a light-chain CDR1 comprising amino acids having the sequence set forth in SEQ ID NO: 4;
  ii) a light-chain CDR2 comprising amino acids having the sequence set forth in SEQ ID NO: 5; and
  iii) a light-chain CDR3 comprising amino acids having the sequence set forth in SEQ ID NO: 6.

2. The antibody-drug conjugate of claim 1, wherein the heavy-chain variable region of the human antibody further comprises cysteine.

3. The antibody-drug conjugate of claim 1, wherein the human antibody is an agonistic antibody against c-Met.

4. The antibody-drug conjugate of claim 1, wherein the human antibody comprises a heavy-chain variable region comprising amino acids having the sequence set forth in SEQ ID NO: 7 or 8 and a light-chain variable region comprising amino acids having the sequence set forth in SEQ ID NO: 11.

5. The antibody-drug conjugate of claim 1, wherein the human antibody comprises a heavy-chain constant region comprising amino acids having the sequence set forth in SEQ ID NO: 13 and a light-chain constant region comprising amino acids having the sequence set forth in SEQ ID NO: 15.

6. The antibody-drug conjugate of claim 1, wherein the cytotoxic, drug is conjugated to the human antibody by a linker.

7. The antibody-drug conjugate of claim 6, wherein the linker is a hydrazone or a peptide linker.

8. The antibody-drug conjugate of claim 1, wherein the cytotoxic drug is conjugated to the human antibody by a Schiff base.

9. The antibody-drug conjugate of claim 6, wherein the cytotoxic drug is conjugated to the human antibody by [linker-Val (valine)-Cit (citrulline)] or [linker-Schiff base].

10. The antibody-drug conjugate of claim 1, wherein the cytotoxic drug is selected from the group consisting of doxorubicin, carboplatin (paraplatin), cisplatin, cyclophosphamide, ifosfamide, nidran, nitrogen mustard (mechlorethamine HCL), Neomycin, mitomycin C, cytarabine, flurouracil, gemcitabine, trimetrexate, methotrexate, etoposide, vinblastine, vinorelbine, alimta, altretamine, procarbazine, taxol, taxotere, topotecan and irinotecan.

11. A pharmaceutical composition for treating cancer that expresses c-Met, which comprises the antibody-drug conjugate of claim 1.

12. The pharmaceutical composition of claim 11, wherein the cancer is a hypoxic tumor.

13. The pharmaceutical composition of claim 11, wherein the conjugate is internalized into cells by endocytosis.

14. The pharmaceutical composition of claim 11, wherein the cytotoxic drug of the conjugate is separated either by intracellular protease or under an intracellular acidic condition.

15. A method for treating cancer that expresses c-Met, which comprises administering the antibody-drug, conjugate of claim 1 to a subject.

16. A method for treating cancer that expresses c-Met, which comprises administering the pharmaceutical composition of claim 11 to a subject.

* * * * *

SEQUENCE LISTING

```
<160> NUMBER OF SEQ ID NOS: 25

<210> SEQ ID NO 1
<211> LENGTH: 5
<212> TYPE: PRT
<213> ORGANISM: Artificial Sequence
<220> FEATURE:
<223> OTHER INFORMATION: CDR1 of a heavy chain variable region

<400> SEQUENCE: 1

Gly His Tyr Trp Ser
 1               5

<210> SEQ ID NO 2
<211> LENGTH: 16
<212> TYPE: PRT
<213> ORGANISM: Artificial Sequence
<220> FEATURE:
<223> OTHER INFORMATION: CDR2 of a heavy chain variable region

<400> SEQUENCE: 2

Glu Ile Ser His Ser Gly Asn Thr Asn Tyr Asn Ser Ser Leu Lys Ser
 1               5                  10                  15

<210> SEQ ID NO 3
<211> LENGTH: 13
```

```
<212> TYPE: PRT
<213> ORGANISM: Artificial Sequence
<220> FEATURE:
<223> OTHER INFORMATION: CDR3 of a heavy chain variable region

<400> SEQUENCE: 3

Phe Tyr Gly Asp Tyr Pro Ser Ser Tyr Gly Met Asp Val
 1               5                  10

<210> SEQ ID NO 4
<211> LENGTH: 14
<212> TYPE: PRT
<213> ORGANISM: Artificial Sequence
<220> FEATURE:
<223> OTHER INFORMATION: CDR1 of a light chain variable region

<400> SEQUENCE: 4

Thr Gly Thr Ile Ser Asp Ile Gly Thr Tyr Asp Phe Val Ser
 1               5                  10

<210> SEQ ID NO 5
<211> LENGTH: 7
<212> TYPE: PRT
<213> ORGANISM: Artificial Sequence
<220> FEATURE:
<223> OTHER INFORMATION: CDR2 of a light chain variable region

<400> SEQUENCE: 5

Asp Val Asn Asn Arg Pro Ser
 1               5

<210> SEQ ID NO 6
<211> LENGTH: 11
<212> TYPE: PRT
<213> ORGANISM: Artificial Sequence
<220> FEATURE:
<223> OTHER INFORMATION: CDR3 of a light chain variable region

<400> SEQUENCE: 6

Ser Ser Tyr Thr Asp Asn Arg Gly Leu Val Leu
 1               5                  10

<210> SEQ ID NO 7
<211> LENGTH: 140
<212> TYPE: PRT
<213> ORGANISM: Artificial Sequence
<220> FEATURE:
<223> OTHER INFORMATION: a heavy chain variable region

<400> SEQUENCE: 7

Met Gly Trp Ser Tyr Ile Ile Leu Phe Leu Val Ala Thr Ala Ala Asp
 1               5                  10                  15

Val His Ser Gln Val Gln Leu Gln Glu Trp Gly Ala Gly Leu Leu Lys
             20                  25                  30

Pro Ser Glu Thr Leu Ser Leu Thr Cys Ala Val Ser Gly Gly Ser Leu
         35                  40                  45

Ser Gly His Tyr Trp Ser Trp Val Arg Leu Pro Pro Gly Lys Gly Leu
     50                  55                  60

Glu Trp Ile Gly Glu Ile Ser His Ser Gly Asn Thr Asn Tyr Asn Ser
 65                  70                  75                  80

Ser Leu Lys Ser Arg Ala Ser Ile Ser Ile Asp Thr Ser Lys Asn Glu
                 85                  90                  95

Tyr Ser Leu Asn Leu Lys Ser Val Thr Ala Val Asp Thr Ala Val Tyr
             100                 105                 110
```

Tyr Cys Ala Arg Phe Tyr Gly Asp Tyr Pro Ser Ser Tyr Gly Met Asp
        115                 120                 125

Val Trp Gly Gln Gly Thr Thr Val Thr Val Ser Ser
    130                 135                 140

<210> SEQ ID NO 8
<211> LENGTH: 141
<212> TYPE: PRT
<213> ORGANISM: Artificial Sequence
<220> FEATURE:
<223> OTHER INFORMATION: a heavy chain variable region with extra
      cysteine

<400> SEQUENCE: 8

Met Gly Trp Ser Tyr Ile Ile Leu Phe Leu Val Ala Thr Ala Ala Asp
  1               5                  10                  15

Val His Ser Gln Val Gln Leu Gln Glu Trp Gly Ala Gly Leu Leu Lys
                 20                  25                  30

Pro Ser Glu Thr Leu Ser Leu Thr Cys Ala Val Ser Gly Gly Ser Leu
            35                  40                  45

Ser Gly His Tyr Trp Ser Trp Val Arg Leu Pro Pro Gly Lys Gly Leu
        50                  55                  60

Glu Trp Ile Gly Glu Ile Ser His Ser Gly Asn Thr Asn Tyr Asn Ser
 65                  70                  75                  80

Ser Leu Lys Ser Arg Ala Ser Ile Ser Ile Asp Thr Ser Lys Asn Glu
                 85                  90                  95

Tyr Ser Leu Asn Leu Lys Ser Val Thr Ala Val Asp Thr Ala Val Tyr
            100                 105                 110

Tyr Cys Ala Arg Phe Tyr Gly Asp Tyr Pro Ser Ser Tyr Gly Met Asp
        115                 120                 125

Val Trp Gly Gln Gly Thr Thr Val Thr Val Ser Ser Cys
    130                 135                 140

<210> SEQ ID NO 9
<211> LENGTH: 420
<212> TYPE: DNA
<213> ORGANISM: Artificial Sequence
<220> FEATURE:
<223> OTHER INFORMATION: a heavy chain variable region

<400> SEQUENCE: 9
atgggatgga gctatatcat cctcttttg gtggccacag cggccgatgt ccactcgcag      60
gtacagctac aggagtgggg cgcaggactg ttgaagcctt cggagaccct gtccctcacc    120
tgcgctgtca gtggtgggtc cctcagtggt cactattgga gctgggtccg tctgcccca    180 gggaagggc tggagtggat tggagaaatc agtcatagtg gtaataccaa ttacaactcg    240
tccctcaaga gtcgagcctc catatccata gacacgtcca agaatgagta ctccttgaac    300
ctgaagtctg tgaccgccgt ggacacggcc gtgtattact gtgcgagatt ctacggtgac    360 taccctctt cttacggtat ggacgtctgg ggccaaggga ccacggtcac cgtctcctca    420

<210> SEQ ID NO 10
<211> LENGTH: 423
<212> TYPE: DNA
<213> ORGANISM: Artificial Sequence
<220> FEATURE:
<223> OTHER INFORMATION: a heavy chain variable region with cysteine

<400> SEQUENCE: 10

```
atgggatgga gctatatcat cctcttttg gtggccacag cggccgatgt ccactcgcag      60
gtacagctac aggagtgggg cgcaggactg ttgaagcctt cggagaccct gtccctcacc     120
tgcgctgtca gtggtgggtc cctcagtggt cactattgga gctgggtccg tctgcccca     180 gggaaggggc tggagtggat tggagaaatc agtcatagtg gtaataccaa ttacaactcg     240
tccctcaaga gtcgagcctc catatccata gacacgtcca agaatgagta ctccttgaac     300
ctgaagtctg tgaccgccgt ggacacggcc gtgtattact gtgcgagatt ctacggtgac     360 taccctctt cttacggtat ggacgtctgg ggccaaggga ccacggtcac cgtctcctca     420
tgc                                                                 423
```

<210> SEQ ID NO 11
<211> LENGTH: 132
<212> TYPE: PRT
<213> ORGANISM: Artificial Sequence
<220> FEATURE:
<223> OTHER INFORMATION: a light chain variable region

<400> SEQUENCE: 11

```
Met Gly Trp Ser Tyr Ile Ile Leu Phe Leu Val Ala Thr Ala Ala Asp
  1               5                  10                  15

Val His Ser Gln Ser Ala Leu Thr Gln Pro Ala Ser Val Ser Gly Ser
             20                  25                  30

Pro Gly Gln Ser Ile Thr Ile Ser Cys Thr Gly Thr Ile Ser Asp Ile
         35                  40                  45

Gly Thr Tyr Asp Phe Val Ser Trp Tyr Gln His Lys Pro Gly Lys Ala
     50                  55                  60

Pro Lys Leu Leu Ile Phe Asp Val Asn Asn Arg Pro Ser Gly Val Ser
 65                  70                  75                  80

Ser Arg Phe Ser Gly Ser Lys Ser Asp Asn Thr Ala Ser Leu Ser Ile
                 85                  90                  95

Ser Gly Phe Gln Ala Glu Asp Glu Ala Asp Tyr Tyr Cys Ser Ser Tyr
            100                 105                 110

Thr Asp Asn Arg Gly Leu Val Leu Phe Gly Gly Gly Thr Lys Leu Thr
        115                 120                 125

Val Leu Arg Ser
        130
```

<210> SEQ ID NO 12
<211> LENGTH: 396
<212> TYPE: DNA
<213> ORGANISM: Artificial Sequence
<220> FEATURE:
<223> OTHER INFORMATION: a light chain variable region

<400> SEQUENCE: 12

```
atgggatgga gctatatcat cctcttttg gtggccacag cggccgatgt ccactcgcag      60
tctgccctga ctcagcctgc ctccgtgtct gggtctcctg gccagtcgat caccatctcc     120
tgcactggaa ccatcagtga cattggcact tatgattttg tctcctggta ccaacataag     180
cccggcaagg cccccaaact cctgattttt gatgtcaata atcggccctc aggggtttct     240
agtcgcttct ctggctccaa gtctgacaat acggcctccc taagcatctc tggattccag     300
gctgaagacg aggctgatta ctactgcagc tcatatacag acaacagagg ccttgtcctt     360
ttcggcggag ggaccaagct gaccgtccta agatct                              396
```

<210> SEQ ID NO 13

<211> LENGTH: 330
<212> TYPE: PRT
<213> ORGANISM: Artificial Sequence
<220> FEATURE:
<223> OTHER INFORMATION: a heavy chain constant region (CH1~CH3)

<400> SEQUENCE: 13

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 14
<211> LENGTH: 990
<212> TYPE: DNA
<213> ORGANISM: Artificial Sequence
<220> FEATURE:
<223> OTHER INFORMATION: a heavy chain constant region (CH1~CH3)

<400> SEQUENCE: 14

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc aacaccaagg tggacaagag agttgagccc     300
aaatcttgtg acaaaactca cacatgccca ccgtgcccag cacctgaact cctgggggga     360
ccgtcagtct tcctctttcc cccaaaaccc aaggacaccc tcatgatctc ccggaccсcct    420
gaggtcacat gcgtggtggt ggacgtgagc cacgaagacc ctgaggtcaa gttcaactgg     480
tacgtggacg gcgtggaggt gcataatgcc aagacaaagc cgcggagga gcagtacaac     540
agcacgtacc gtgtggtcag cgtcctcacc gtcctgcacc aggactggct gaatggcaag     600
gagtacaagt gcaaggtctc caacaaagcc ctcccagccc ccatcgagaa aaccatctcc     660
aaagccaaag ggcagccccg agaaccacag gtgtacaccc tgcccccatc ccgggatgag     720
ctgaccaaga accaggtcag cctgacctgc ctggtcaaag gcttctatcc cagcgacatc     780
gccgtggagt gggagagcaa tgggcagccg gagaacaact acaagaccac gcctcccgtg     840
ctggactccg acggctcctt cttcctctac agcaagctca ccgtggacaa gagcaggtgg     900
cagcagggga acgtcttctc atgctccgtg atgcatgagg ctctgcacaa ccactacacg     960
cagaagagcc tctccctgtc tccgggtaaa                                      990
```

<210> SEQ ID NO 15
<211> LENGTH: 105
<212> TYPE: PRT
<213> ORGANISM: Artificial Sequence
<220> FEATURE:
<223> OTHER INFORMATION: a light chain constant region

<400> SEQUENCE: 15

```
Val Ala Ala Pro Ser Val Phe Ile Phe Pro Pro Ser Asp Glu Gln Leu
 1               5                  10                  15
Lys Ser Gly Thr Ala Ser Val Val Cys Leu Leu Asn Asn Phe Tyr Pro
             20                  25                  30
Arg Glu Ala Lys Val Gln Trp Lys Val Asp Asn Ala Leu Gln Ser Gly
         35                  40                  45
Asn Ser Gln Glu Ser Val Thr Glu Gln Asp Ser Lys Asp Ser Thr Tyr
     50                  55                  60
Ser Leu Ser Ser Thr Leu Thr Leu Ser Lys Ala Asp Tyr Glu Lys His
 65                  70                  75                  80
Lys Val Tyr Ala Cys Glu Val Thr His Gln Gly Leu Ser Ser Pro Val
                 85                  90                  95
Thr Lys Ser Phe Asn Arg Gly Glu Cys
            100                 105
```

<210> SEQ ID NO 16
<211> LENGTH: 315
<212> TYPE: DNA
<213> ORGANISM: Artificial Sequence
<220> FEATURE:
<223> OTHER INFORMATION: a light chain constant region

<400> SEQUENCE: 16

```
gtggctgcac catctgtctt catcttcccg ccatctgatg agcagttgaa atctggaact      60
```

| | |
|---|---|
| gcctctgttg tgtgcctgct gaataacttc tatcccagag aggccaaagt acagtggaag | 120 |
| gtggataacg ccctccaatc gggtaactcc caggagagtg tcacagagca ggacagcaag | 180 |
| gacagcacct acagcctcag cagcaccctg acgctgagca aagcagacta cgagaaacac | 240 |
| aaagtctacg cctgcgaagt cacccatcag ggcctgagct cgcccgtcac aaagagcttc | 300 |
| aacaggggag agtgt | 315 |

<210> SEQ ID NO 17
<211> LENGTH: 20
<212> TYPE: DNA
<213> ORGANISM: Artificial Sequence
<220> FEATURE:
<223> OTHER INFORMATION: pYG100-F primer

<400> SEQUENCE: 17
cagctatgac catgattacg                     20

<210> SEQ ID NO 18
<211> LENGTH: 20
<212> TYPE: DNA
<213> ORGANISM: Artificial Sequence
<220> FEATURE:
<223> OTHER INFORMATION: pYG100-R primer

<400> SEQUENCE: 18
cttattagcg tttgccatct                     20

<210> SEQ ID NO 19
<211> LENGTH: 50
<212> TYPE: DNA
<213> ORGANISM: Artificial Sequence
<220> FEATURE:
<223> OTHER INFORMATION: NATVH4-2 primer

<400> SEQUENCE: 19
ttggtggcca cagcggccga tgtccactcg caggtgcagc tacagcagtg           50

<210> SEQ ID NO 20
<211> LENGTH: 26
<212> TYPE: DNA
<213> ORGANISM: Artificial Sequence
<220> FEATURE:
<223> OTHER INFORMATION: NATJH-ALL NheI primer

<400> SEQUENCE: 20
gaggaggcta gctgaggaga cggtga                     26

<210> SEQ ID NO 21
<211> LENGTH: 50
<212> TYPE: DNA
<213> ORGANISM: Artificial Sequence
<220> FEATURE:
<223> OTHER INFORMATION: NATVL4 primer

<400> SEQUENCE: 21
ttggtggcca cagcggccga tgtccactcg cagtctgccc tgactcagcc           50

<210> SEQ ID NO 22
<211> LENGTH: 33
<212> TYPE: DNA
<213> ORGANISM: Artificial Sequence
<220> FEATURE:
<223> OTHER INFORMATION: NATJL2-R primer

<400> SEQUENCE: 22

```
gaggagagat cttaggacgg tcagcttggt ccc                                    33

<210> SEQ ID NO 23
<211> LENGTH: 18
<212> TYPE: DNA
<213> ORGANISM: Artificial Sequence
<220> FEATURE:
<223> OTHER INFORMATION: CMV-proF primer

<400> SEQUENCE: 23
aaatgggcgg taggcgtg                                                     18

<210> SEQ ID NO 24
<211> LENGTH: 50
<212> TYPE: DNA
<213> ORGANISM: Artificial Sequence
<220> FEATURE:
<223> OTHER INFORMATION: Forward primer

<400> SEQUENCE: 24
ttggtggcca cagcggccga tgtccactcg caggtacagc tacaggagtg                  50

<210> SEQ ID NO 25
<211> LENGTH: 29
<212> TYPE: DNA
<213> ORGANISM: Artificial Sequence
<220> FEATURE:
<223> OTHER INFORMATION: Reverse primer

<400> SEQUENCE: 25
gaggaggcta gcgcatgagg agacggtga                                         29
```